US012788539B2

(12) United States Patent
Jensen et al.

(10) Patent No.: US 12,788,539 B2
(45) Date of Patent: Nov. 10, 2026

(54) SYSTEM AND METHOD FOR PROVIDING DYNAMIC FEEDBACK DURING SCANNING OF A DENTAL OBJECT

(71) Applicant: 3SHAPE A/S, Copenhagen K (DK)

(72) Inventors: Peter Dahl Ejby Jensen, Copenhagen K (DK); Simon Hoffgaard, Copenhagen K (DK); Anders Sindal Stæhr, Copenhagen K (DK)

(73) Assignee: 3SHAPE A/S, Copenhagen K (DK)

( * ) Notice: Subject to any disclaimer, the term of this patent is extended or adjusted under 35 U.S.C. 154(b) by 692 days.

(21) Appl. No.: 18/311,622

(22) Filed: May 3, 2023

(65) Prior Publication Data

US 2023/0355360 A1 Nov. 9, 2023

(30) Foreign Application Priority Data

May 4, 2022 (EP) .................................... 22171602

(51) Int. Cl.
*A61C 9/00* (2006.01)
*A61B 34/10* (2016.01)
*G06T 7/00* (2017.01)

(52) U.S. Cl.
CPC ............ *A61C 9/0053* (2013.01); *A61B 34/10* (2016.02); *G06T 7/0016* (2013.01); *A61B 2034/102* (2016.02)

(58) Field of Classification Search
CPC ... A61C 9/0053; G06T 7/0016; A61B 5/4547; A61B 5/7415; A61B 5/7455
See application file for complete search history.

(56) References Cited

U.S. PATENT DOCUMENTS

| | | | | |
|---|---|---|---|---|
| 12,508,114 B2* | 12/2025 | Pesach | .................. | A61C 19/04 |
| 2008/0038688 A1 | 2/2008 | Kopelman et al. | | |
| 2012/0141949 A1 | 6/2012 | Bodony et al. | | |
| 2015/0221084 A1* | 8/2015 | Adamson | ........... | A61B 1/00009 348/46 |

(Continued)

FOREIGN PATENT DOCUMENTS

| | | | |
|---|---|---|---|
| EP | 3689218 A1 | 8/2020 | |
| WO | 2022020267 A1 | 1/2022 | |

*Primary Examiner* — Benjamin O Dulaney
(74) *Attorney, Agent, or Firm* — Buchanan Ingersoll & Rooney PC

(57) ABSTRACT

The present disclosure relates to a computer-implemented method for providing feedback during scanning of a dental object, comprising the steps of obtaining scan data of the dental object; generating a digital three-dimensional (3D) representation of the dental object based on the scan data; obtaining new scan data of the dental object; generating an updated digital 3D representation by adding the new scan data to the digital 3D representation; determining added information to the digital 3D representation by comparing the new scan data to at least one of the digital 3D representation(s) and/or by comparing the updated digital 3D representation to the digital 3D representation(s); and providing a feedback signal; wherein the feedback signal correlates with the added information and/or a determined overlap. The present disclosure further relates to a 3D scanner system and a handheld intraoral scanning device, configured for providing the feedback signal such as by executing the computer-implemented method.

21 Claims, 8 Drawing Sheets

(56) References Cited

U.S. PATENT DOCUMENTS

| | | | | |
|---|---|---|---|---|
| 2016/0051345 | A1* | 2/2016 | Levin | A61C 9/0053<br>433/29 |
| 2016/0051348 | A1* | 2/2016 | Boerjes | A61C 11/08<br>433/215 |
| 2017/0215698 | A1* | 8/2017 | Rynerson | A61B 1/00048 |
| 2020/0214538 | A1* | 7/2020 | Pesach | A61C 19/04 |
| 2022/0241056 | A1* | 8/2022 | Salah | A61B 1/000094 |
| 2023/0021695 | A1* | 1/2023 | Atiya | A61C 9/0053 |
| 2025/0041030 | A1* | 2/2025 | Elbaz | A61B 1/046 |

* cited by examiner

SYSTEM AND METHOD FOR PROVIDING DYNAMIC FEEDBACK DURING SCANNING OF A DENTAL OBJECT

TECHNICAL FIELD

The present disclosure relates to a system and computer-implemented method for providing feedback during scanning of a dental object. The disclosure further relates to a 3D scanner system for providing said feedback and an intraoral scanning device.

BACKGROUND

Three-dimensional (3D) representation is relevant in many fields such as medicine or civil engineering. In dentistry, a 3D digital representation of a dental object represents a clear advantage to help dentists give the best treatment to a patient. Indeed, digital dentistry gives the opportunity of expanding dentist expertise with new treatment options and provides possibilities for more cost-effective ways of taking care of their patients.

Intraoral scanners are devices for capturing a digital impression of a patient's dentition within dentistry. In a typical scanning scenario using a handheld intraoral scanning device, a digital 3D representation is reconstructed in real-time and simultaneously rendered to a display to provide visual guidance and user feedback to the user via the display. This implies that the user needs to focus on a display to see whether he/she is progressing in their scanning as the 3D representation is constructed in real-time on the display providing visual feedback on the progress and data coverages.

This method is not ideal as it shifts the focus of the user away from the patient by drawing attention to the display. State of the art intraoral scanning devices are additionally becoming more than a digital impression tool as diagnostic capabilities are added to the scanners to capture more information than surface information. Some of this additional information, like infrared images or fluorescence images is typically captured in real-time, but not displayed in real-time. Hence, the dentist does not have any feedback on data quality or data coverage of the diagnostic data. Hence, there is a desire to provide another type of feedback which provides the user with information on data coverage or data quality. Furthermore, it is desired to develop feedback outside of the graphical user interface such that the user can focus more on the patient.

SUMMARY

As disclosed herein, the above-mentioned challenges are addressed by providing a computer-implemented method for providing feedback during scanning of a dental object, the method comprising the steps of:

- obtaining current scan data of the dental object;
- generating a digital three-dimensional (3D) representation of the dental object based on the current scan data;
- obtaining new scan data of the dental object;
- generating an updated digital 3D representation by adding the new scan data to the digital 3D representation;
- determining added information to the digital 3D representation by comparing the new scan data to at least one of the digital 3D representation(s) and/or by comparing the updated digital 3D representation to the digital 3D representation(s); and
- providing a feedback signal.

The feedback signal may correlate to the added information, which can be determined in a step of the computer-implemented method, as previously described.

As described previously, users may in many cases have to focus on the digital 3D representation displayed through a GUI while scanning, instead of focusing their time on the patient and the scanner. This leads to a situation where the dentist is maneuvering the scanner around in the oral cavity of the patient while looking at a screen. This can generate longer time to scan dental objects as the maneuvering of the scanner may lead over areas which have already been scanned. Additionally, the dentist tends to move the scanner much slower than needed, which both increases scan time and at the same time, increases the amount of scan data acquired during scanning, which may result in a prolonged processing time and may even slow down the performance of the processor responsible for constructing the 3D digital representation from the scan data. By introducing this dynamic feedback signal provided by the computer-implement method, it is possible to assist the user to avoid wasting time by scanning the same area for too long, avoiding overloading the processors with scan data and simultaneously enables the user to focus more on the dental object to be scanned and more generally on the patient.

The computer-implemented method provides a feedback signal which is configured to provide guidance to the user about the information received while scanning a dental object. Accordingly, this could for example be information that a new area is being scanned. However, on the contrary it could also be information that nothing new is being scanned so that the user can move the scanner to scan another area. Because the feedback signal is correlated to the added information to the digital 3D representation, the user can get an indication on how much information is added to the digital 3D representation while scanning a dental object.

In one aspect, a 3D scanner system for scanning a dental object comprises an intraoral scanning device, comprising at least one optical sensor for obtaining scan data of the dental object and one or more processing unit(s) configured to continuously performing the steps of:

- generating a digital three-dimensional (3D) representation of the dental object based on the scan data;
- obtaining new scan data of the dental object;
- generating an updated digital 3D representation by adding the new scan data to the digital 3D representation;
- determining added information to the digital 3D representation by comparing the new scan data to at least one of the digital 3D representation(s); and
- providing a feedback signal, wherein the feedback signal correlates with the added information.

In some embodiments, the 3D scanner system comprises:

- an intraoral scanning device for scanning a dental object within an oral cavity of a patient, the intraoral scanning device comprising:
  - one or more projector units for projecting a pattern of light onto a surface of the dental object;
  - one or more image sensors for acquiring one or more images in response to illuminating the surface of the dental object;
- one or more processing units operatively coupled to the intraoral scanning device, the processing unit(s) configured for performing the steps of:
  - generating a first digital three-dimensional (3D) representation of the dental object based on the acquired image(s);

updating the digital 3D representation based on the acquisition of one or more subsequently acquired image(s), whereby a second digital 3D representation is generated; and determining an amount of overlap between the first and the second digital 3D representations;

wherein the 3D scanner system is configured for providing a feedback signal correlating with the amount of overlap, wherein the feedback signal is an auditory signal comprising a plurality of sound pulses separated by a time delay, wherein the time delay is changed based on the determined overlap.

In some embodiments, the 3D scanner system comprises:

an intraoral scanning device for scanning a dental object within an oral cavity of a patient, the intraoral scanning device comprising:

one or more projector units for projecting a pattern of light onto a surface of the dental object;

one or more image sensors for acquiring one or more images in response to illuminating a surface of the dental object, wherein the dental object is at least a part of a dental arch;

one or more processing units operatively coupled to the intraoral scanning device, the processing unit(s) configured for continuously, during a scanning session, performing the steps of:

generating a digital three-dimensional (3D) representation of the dental object based on one or more scan patches, wherein the scan patches are generated based on images acquired by the image sensor(s);

updating the digital 3D representation based on registration of one or more new scan patches to said 3D representation, wherein said new scan patches at least partially overlap with the digital 3D representation; and determining the amount of overlap between the digital 3D representation and the new scan patch(es);

wherein the 3D scanner system is configured for providing a feedback signal correlating with the amount of overlap, wherein the feedback signal is an auditory signal comprising a plurality of sound pulses separated by a time delay, wherein the 3D scanner system is configured for changing the time delay based on the determined overlap.

In some embodiments, the 3D scanner system comprises:

an intraoral scanning device for scanning a dental object within an oral cavity of a patient, the intraoral scanning device comprising:

one or more projector units for projecting a pattern of light onto a surface of the dental object;

one or more image sensors for acquiring one or more images in response to illuminating the surface of the dental object;

a light-emitting device configured for providing a visual feedback signal to a user operating the intraoral scanning device;

one or more processing units operatively coupled to the intraoral scanning device, the processing unit(s) being configured for performing the steps of:

generating a first digital three-dimensional (3D) representation of the dental object based on the acquired image(s);

updating the digital 3D representation based on the acquisition of one or more subsequently acquired image(s), whereby a second digital 3D representation is generated;

determining an amount of overlap between the first and the second digital 3D representations;

wherein the visual feedback signal correlates with the amount of overlap, and wherein the light-emitting device is configured for changing a brightness level of the visual feedback signal based on the determined overlap.

The aforementioned embodiments may be combined such that both an auditory feedback signal and a visual feedback signal is provided to the user during a scanning session.

Preferably, the steps of the computer-implemented method as disclosed herein are performed continuously and/or in real-time. The 3D scanner system for scanning a dental object may further comprise at least one output device for providing an output to a user during scanning, where the output is based on the feedback signal provided by the computer-implemented method.

In yet another aspect, a handheld intraoral scanning device, comprising a scanner housing configured to be handled with one hand, wherein the scanner housing comprises:

an optical sensor for obtaining scan data of a dental object;

one or more processing unit(s) for processing the scan data; and one or more output device(s) for providing an output to a user.

The handheld intraoral scanning device is configured to receive at least one feedback signal provided by the computer-implemented method and to provide the output to the user from the one or more output device(s) based on the at least one feedback signal.

The feedback signal as discussed in the aspects above, and as generally discussed in the disclosure, is typically output by at least one output device, wherein the at least one output device may be an audio device and/or a haptic device and/or a light-emitting device. In some embodiments, the 3D scanner system comprises a haptic device configured for providing a haptic feedback signal. Preferably, the haptic device is located in the intraoral scanning device. In some embodiments, at least a property of the haptic feedback signal is altered based on the added information and/or the determined overlap. As an example, a vibration level of the haptic device may be increased when the determined overlap is below a predefined lower threshold, and the vibration level may be decreased when the determined overlap is above a predefined upper threshold. An advantage of an intraoral scanning device comprising a haptic device is that the user can receive a non-visible feedback, e.g. by feeling a vibration in the scanning device, if the scanning can be improved. Thus, the user can correct the way he uses the scanning device immediately based on the feedback. In some embodiments, several different types of feedback are provided. As an example, the scanning device may comprise a light-emitting device for providing a visual feedback correlated to the added data and/or the determined overlap, and the scanning device may further comprise a haptic device as previously mentioned. Additionally, in some embodiments the scanning device comprises a speaker for outputting an audible feedback signal as described further herein. In other embodiments, the 3D scanner system comprises an external speaker, i.e. a speaker which is not located on the intraoral scanning device.

In a preferred embodiment, the computer-implemented method for providing feedback during scanning of a dental object, comprises the steps of:

obtaining scan data of the dental object;

generating a digital three-dimensional (3D) representation of the dental object based on the scan data;

obtaining new scan data of the dental object;

updating the digital 3D representation based on the new scan data;

determining added information to the digital 3D representation by comparing the new scan data to the digital 3D representation and/or by comparing the updated digital 3D representation to the digital 3D representation; and providing a feedback signal, wherein the feedback signal correlates with the added information.

Preferably, the steps of the computer-implemented method as disclosed herein are performed continuously and/or in real-time. An advantage of updating the digital 3D representation and providing a feedback signal in real-time is that the user, e.g. the dentist, can immediately react according to the feedback signal. In other words, if the user for example scans too slowly, the user is preferably notified by the feedback signal in real-time, such that the user can correct his action(s) and e.g. scan faster. If the user holds the scanning device extensively over the same area of the dental object, i.e. such that an excessive overlap between the 3D representation and new scan patches occurs, the user is advantageously notified by the feedback signal as disclosed herein. Preferably, the feedback signal correlates with the amount of overlap between the 3D representation and new scan data/new scan patches, such that the user is encouraged to move the scanning device and scan new areas of the dental object. Another example is if the registration of new scan patches is lost, i.e. if the new scan data/scan patch cannot be registered/added to the digital 3D representation, then the user should preferably be notified in real-time by the feedback signal, e.g. either by a visual feedback, an audible feedback, or a haptic feedback.

The disclosure further relates to an 3D scanner system for scanning a dental object, wherein the scanner system comprises: an intraoral scanning device; and one or more processing unit(s) configured to carry out the computer-implemented method as disclosed herein.

DETAILED DESCRIPTION

Figure 1:
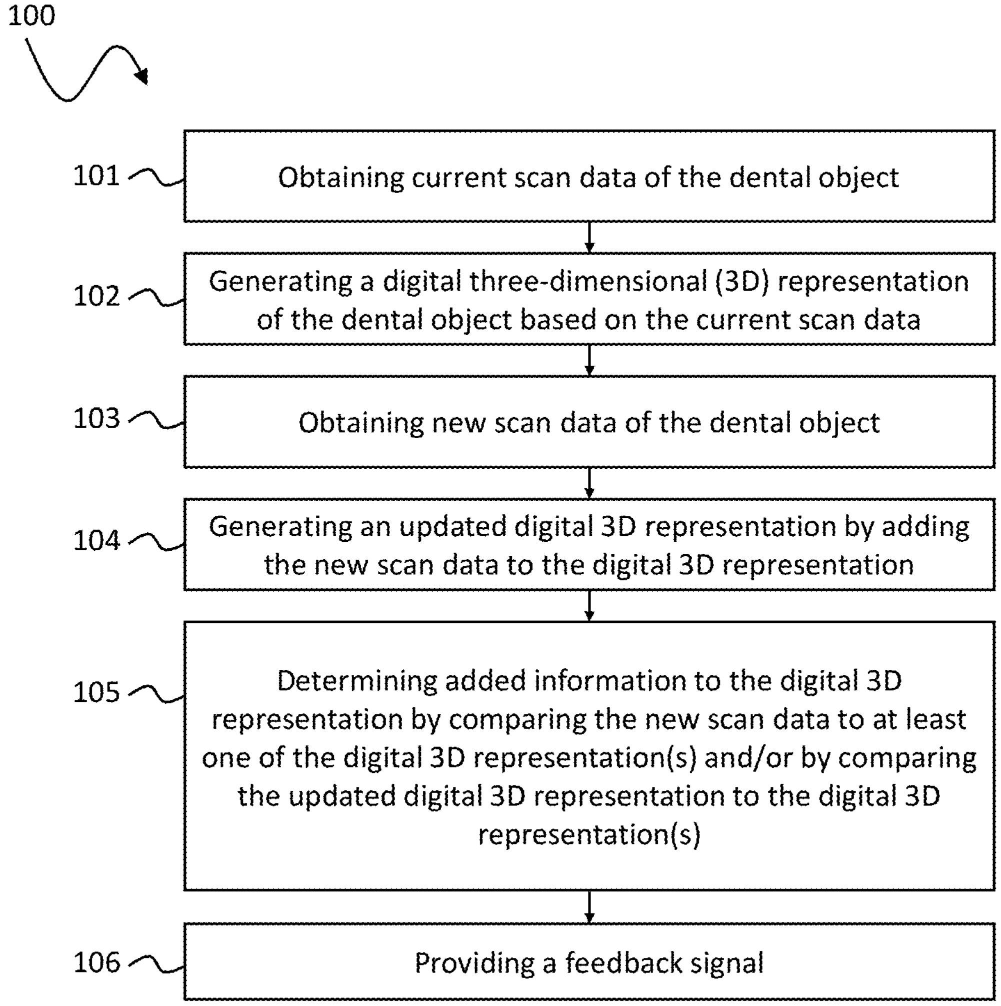
FIG. 1 shows a flow-chart of an embodiment of the computer-implemented method according to the present disclosure.

In an embodiment, a handheld 3D scanner is a device which may produce scan data. Scan data may comprise surface information in the form of point clouds, a sequence of images, or one or more scan patches. Each point in the cloud may be a result of a distance measurement in the view direction of the scanner. The coordinates of the point may be relative to a coordinate system fixed to the scanner, which can denote a local frame.

The scanning device may be a focus scanner which uses moving lenses to sweep a narrow focus band through the scanners field of view, which may then be referred to as the scan volume. The scanning device is operated by projecting a pattern and translating a focus plane along an optical axis of the scanning device and capturing a plurality of 2D images at different focus plane positions such that each series of captured 2D images corresponding to each focus plane forms a stack of 2D images. The acquired 2D images are also referred to herein as raw 2D images, wherein raw in this context means that the images have not been subject to image processing. The focus plane position is shifted along the optical axis of the scanning system, such that 2D images captured at a number of focus plane positions along the optical axis form said stack of 2D images for a given view of the object, i.e. for a given arrangement of the scanning system relative to the object. Once a physical object is in focus it's distance to the scanner (in the view direction) can be computed from knowledge of the position of the focus band and the geometry of the scanner.

The intraoral scanning device may be based on other scanning principle such as triangulation-based scanning, confocal scanning, focus scanning, ultrasound scanning, x-ray scanning, stereo vision, structure from motion, optical coherent tomography (OCT), or any other scanning principle A scanning session may be understood herein as a period of time during which data (such as image data, depth data, 3D data, scan patches, color data, or combinations thereof) of a three-dimensional dental object is acquired using the 3D scanner system. During a scanning session the scanner, and hence the local frames, move relative to a fixed global coordinate frame of the scene which may be a dental object such as the dentition of a patient. The result is a sequence of scan patches recorded at discrete times. The scanner may additionally use external tracking, such as a motion or a position sensor to achieve a priori knowledge of the pose of the scanner as part of the scan data. The frame rate of the intraoral scanning device may be high relative to the movement of physical scanning device such that consecutive scan patches have substantial overlap.

Hence, the amount of overlap typically depends on the frame rate of the scanner and the movement. Typically, a registration algorithm is used to first align and/or register the incoming scan data/scan patches to the current 3D representation, then fuse the new scan patch with the 3D representation and finally render the fused 3D representation on a screen before the next scan patch arrives from the scanner. Accordingly, the step of updating the digital 3D representation preferably comprises registering the new scan data/scan patch to the digital 3D representation. The computer-implemented method may further comprise a step of fusing the new scan data/scan patch to the digital 3D representation. Registration/registering new scan data/scan patch should be understood as determining the location of said scan patch in the (current) digital 3D representation, whereas fusion/fusing the scan data/scan patch should be understood as making said scan data/scan patch a part of the digital 3D representation. For the registration of scan patches a variant of the Iterated Closest Point (ICP) algorithm may be used.

In one embodiment, scan data may be understood as any type of data recorded by the intraoral scanning device. Scan data may typically comprise surface information such as a point cloud or a scan patch as described above providing information about the morphology and structure of the dental object. However, scan data may contain additional data associated with the dental object. Such information may be reflected color texture information, representing the color of the dental object from the direction observed by the scanner. Other information could be a fluorescence texture response recorded from the dental object when exposed to a wavelength capable of exciting a fluorescence response from the dental material. Infrared or near infrared light are examples of wavelength ranges which may provide information related to the internal structure of the dental object such as the enamel/dentin junction, cracks or caries lesions inside the tooth. Scan data may additionally comprise processed information based on the information received directly from the scanner, such information could be shade values associated with the dental object, diagnostic scoring information or data quality check information.

A digital 3D representation should be understood as a point cloud, a point cloud with additional attributes like point normals, point colors, a triangulated point cloud (a triangle mesh), a polygonal mesh, a volumetric representation/voxel model, parametric representations, e.g. a spline representation. The digital 3D representation may additionally include a virtual representation of an object in three dimensions in which internal regions (structures, etc.) are arranged within the volume in three physical dimensions in proportion and relative to the other internal and surface features of the object which is being modelled. For example, a volumetric representation of a tooth may include the outer surface as well as internal structures within the tooth (beneath the tooth surface) proportionately arranged relative to the tooth, so that a section through the volumetric model would substantially correspond to a section through the tooth, showing position and size of internal structures.

A feedback signal should be understood herein as a signal provided to an output device for providing feedback (information) to a user. Alternatively, a feedback signal may simply refer to the actual feedback provided to the user during a scanning session. The feedback may relate to a variety of information related to scanning the dental object. Examples include whether scan data is acquired, the rate of which new scan data is acquired, whether scan patches are correctly registered, if registration of scan patches are unsuccessful, the progress of the scanning, whether the dental object is completely scanned, etc. Other information given as feedback may be envisioned without departing from the scope of the present disclosure.

In preferred embodiments, the feedback signal and/or the feedback is correlated to the rate of which new scan data is acquired or to the amount of added data. The added data may be determined by comparing scan data associated with a first and second 3D representation or by comparing second scan data to the first 3D representation or by comparing first and second scan data. Accordingly, the user should be able to (qualitatively) tell from the feedback signal/feedback the rate (high/low) of new data being acquired or the amount (high/low) of added data. Therefore, preferably the feedback is altered dynamically, preferably in real-time, during a scanning session, wherein the alteration/change reflects the change in the amount of added data and/or the change in the rate of new data acquired. New data should be understood herein as data covering new areas/surfaces of the dental object, which does not form part of the existing 3D representation. In other words, the presently disclosed system and method(s) provide a framework for providing dynamic feedback to the user during a scanning session, wherein the feedback is adjusted/altered based on the rate of which new scan data is acquired or based on the amount of new scan data/added data.

In preferred embodiments, the 3D scanner system comprises an output device for providing feedback as described herein. As an example, the output device may be configured to receive a feedback signal, which is modulated based on e.g. the rate of which new scan data is acquired. The output device may then further be configured to provide feedback to the user, e.g. in the form of audible feedback, tactile feedback, or visible feedback. Examples of suitable output devices include speaker(s), vibrating unit(s), and light source(s). Some embodiments of the 3D scanner system comprise multiple output devices. In some embodiments, the intraoral scanning device comprises a vibrating unit and a light source, such as an LED ring around the circumference of the scanning device. As an example, the light source may be configured to increase/decrease in brightness depending on the rate of which new scan data is acquired or depending on whether scan patches are correctly registered.

In preferred embodiments, at least one type of feedback is provided as a sound/audible signal. In preferred embodiments, the 3D scanner system comprises a speaker for providing the sound. In some embodiments, the speaker is external to the intraoral scanning device. In other embodiments, the intraoral scanning device comprises a speaker. In preferred embodiments, the sound comprises a plurality of sound pulses separated by a temporal distance (e.g. a time delay), i.e. the time between two pulses.

In some embodiments, the feedback signal is an auditory signal comprising a plurality of sound pulses separated by a time delay, wherein the time delay is changed based on the determined overlap. As an example, the time delay may be increased when the determined overlap is below a predefined lower threshold, and the time delay may be decreased when the determined overlap is above a predefined upper threshold. As another example, the time delay may be selected from a predefined first range when the determined overlap is above a predefined upper threshold, and the time delay may further be selected from a predefined second range when the determined overlap is below a predefined lower threshold. Preferably, the low end of the predefined second range is above the low end of the predefined first range. In some embodiments, the predefined first range covers the range 10 ms to 150 ms, such as 20 ms to 130 ms, such as 30 ms to 110 ms, and the predefined second range covers the range 50 ms to 250 ms, such as 60 ms to 200 ms, such as 70 ms to 150 ms. In some embodiments, the time delay is randomly generated within said first and second ranges. In experiments performed by the inventors, said first and second ranges were found particularly useful in providing feedback to the user, which could be intuitively understood by the user. One reason is that the sound of the auditory signal is familiar to vacuum cleaning over a plurality of smaller objects, e.g. sand or small stones, which creates a sound that depends on how fast the vacuum cleaner is moved across the objects. The 'nudging effect' is thus closely correlated with the choice of time delay between the sound pulses in the auditory signal.

The plurality of sound pulses may be experienced by the user as a ticking or clicking sound. As an example of how the feedback (here sound) may be correlated to the rate of which new scan data is acquired or correlated to the amount of new scan data/added data, the temporal distance between the sound pulses may be adjusted, preferably continuously and/or in real-time during the scanning session, such that the distance shortens when the amount of new scan data/added data is high. A high amount of new scan data may be understood as scan data (e.g. provided as a scan patch) having a small overlap with the existing 3D representation, i.e. scan data that covers at least some area which has not yet been imaged during said scanning session. Similarly, the sound may be adjusted by lengthening the temporal distance between the sound pulses, if the amount of new scan data/added data is low, i.e. if the new scan data has a high overlap with the existing 3D representation.

FIG. 1 shows a flow-chart of an embodiment of the computer-implemented method (100) disclosed herein. In this embodiment, the computer-implemented method (100) for providing feedback comprises the steps of:

- obtaining current scan data of the dental object (101);
- generating a digital three-dimensional (3D) representation of the dental object based on the current scan data (102);
- obtaining new scan data of the dental object (103);
- generating an updated digital 3D representation by adding the new scan data to the digital 3D representation (104);
- determining added information to the digital 3D representation by comparing the new scan data to at least one of the digital 3D representation(s) and/or by comparing the updated digital 3D representation to the digital 3D representation(s) (105); and
- providing a feedback signal (106).

Figure 4:
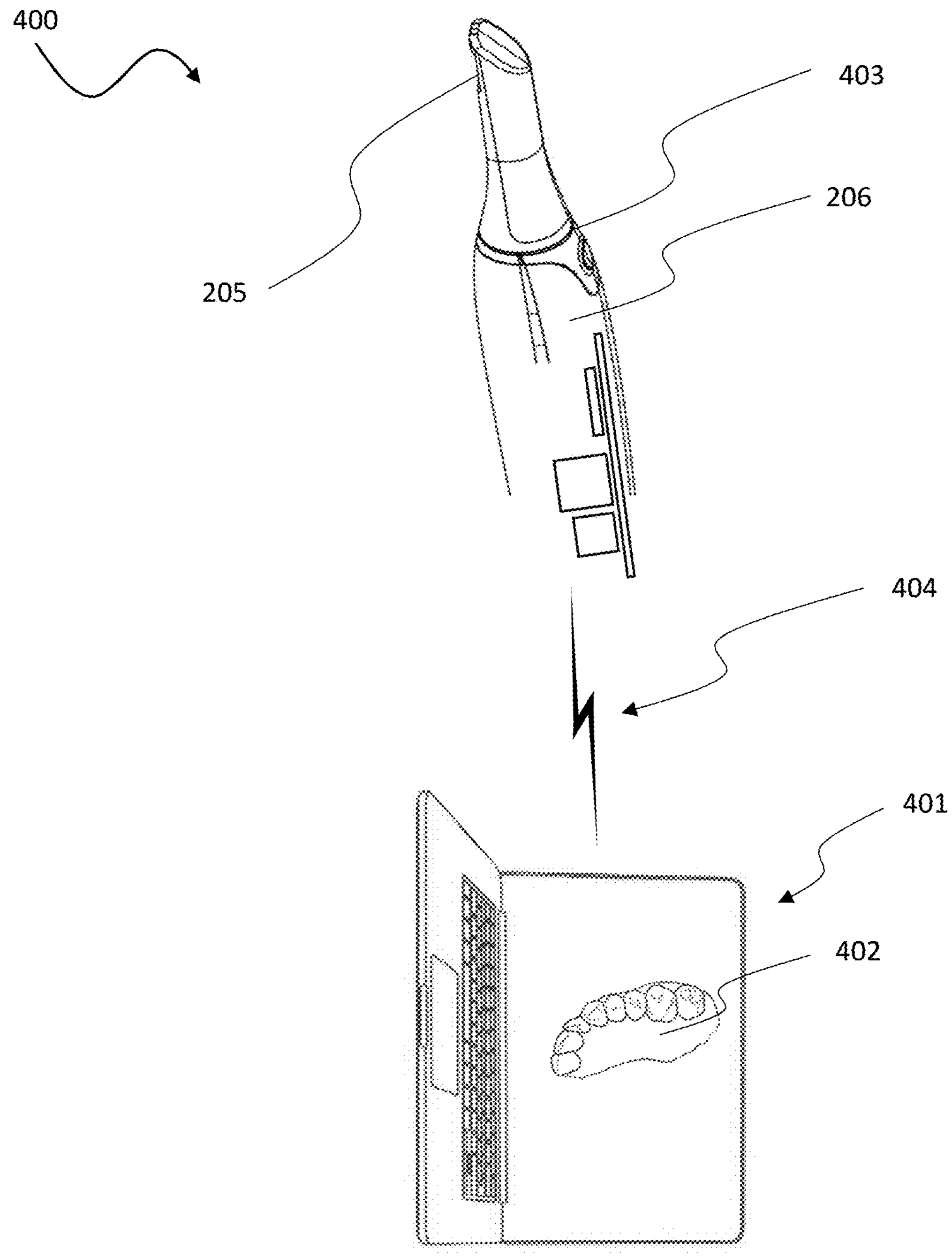
FIG. 4 shows a perspective view of an embodiment of a 3D scanner system for scanning a dental object.

Obtaining current scan data of the dental object (101) is the first step of the computer-implemented method (100) and can be performed with a 3D scanner system, as shown in FIG. 4, where a 3D scanner system (400) is presented. A user of the 3D scanner system (400) can obtain current scan data of the dental object by scanning a dental object with an intraoral scanning device comprised in the 3D scanner system (400). During the scanning of the dental object, a digital 3D representation (402) of the dental object may be generated, e.g. continuously generated in real-time, based on what the user is scanning. Since the scanning of the dental object may be continuously performed, new scan data can subsequently obtained.

The new scan data may generate an updated digital 3D representation by adding the new scan data to the digital 3D representation. Added information to the digital 3D representation can then be determined by comparing the new scan data to at least one of the digital 3D representation(s) and/or by comparing the updated digital 3D representation to the digital 3D representation(s). Based on the added information determined in the previous step, a feedback signal can be provided. In some embodiments, the step of determining added information comprises comparing the new scan data to the digital 3D representation, wherein said comparison comprises determining an overlap between the new scan data and the digital 3D representation.

The digital 3D representation (402) can be a three-dimensional representation of the object to be scanned. This object may be a dental object such as the patient's dentition. The digital 3D representation (402) can be generated based on the scan data. The scan data may be based on a processed group of images acquired by at least one image sensor, which can be comprised in an intraoral scanning device and which may be further comprised in the 3D scanner system (400).

The feedback signal is preferably correlated with the added information. In preferred embodiments, at least a property of the feedback signal is altered based on the determined overlap. In some embodiments, the property of the feedback signal is selected from the group of: frequency, amplitude, pitch, time delay between pulses of the signal, and/or combinations thereof. In other embodiments, the property of the feedback signal is selected from the group of: brightness level, vibration level, color of emitted light, and/or combinations thereof.

In particular, the feedback signal may be modulated depending on the added information. As previously discussed, providing a feedback signal while scanning facilitates scanning and creates an improved scanning experience. Additionally, the data quality may be improved. Time wasted by scanning the same area for too long is reduced and it can also help keeping the user's focus more on the dental object to be scanned and more generally on the patient while simultaneously avoiding overloading the processors.

A dentist will typically be scanning the patient continuously as the scanner is moved to cover the dental object. Accordingly, in order to provide a further improved scanning experience, one or more of the step(s) of the computer-implemented method (100) may in one embodiment be continuously performed during scanning of the dental object.

The added information is a parameter/value/representation which describes new relevant information added to an existing 3D representation. Thus, the information representing the added information may vary depending on the desired information obtained and the form in which the added information is stored. E.g. the added information may be understood as any added information provided by the scan data. Examples may be added surface data or an added texture data etc. Added data may be evaluated as a difference between new scan data and old scan data. Old scan data should be understood as scan data, which forms part of the 3D representation. Differences may be evaluated as an Euclidean distance in color space such as RGB or LAB colors. Added volumetric data, such as additional information related to the internal structures of the dental object. Added data as additional information related to surface properties like roughness or scattering properties or a combination hereof. In other words, added information should be understood as a difference or discrepancy in one or more characteristics between new scan data and existing scan data.

In one embodiment, the intraoral scanning device may acquire scan data as a combination of different modalities, such as reflected light information to obtain surface information and infra-light information to obtain information data of the internal structure of the dental object, such as enamel-dentin junction, cracks or caries. In such a scenario, some scan data information may not be visible to the user during the real time acquisition via the display, hence the scanning device and associated method disclosed herein is particular advantageous as feedback is provided to the user during scanning such that high quality data can be obtained. Internal structures of the dental object may be imaged with IR, near-IR light or any appropriate wavelength which make the dentition appear semi-transparent. For example, deep red light in the range 600 nm to 750 nm, or near infrared light in the range of 700 nm to 1090 nm (e.g., 850 nm) may be used. Other wavelengths and ranges of wavelengths may be used, including wavelengths shorter than the visible spectrum.

In another embodiment, the intraoral scanning device may acquire scan data comprising surface information, while the computer-implemented method is performed completely without a display to render the 3D representation real-time. In such a scenario, no visual guidance or feedback is provided by the display thus it is particular advantageous to provide dynamic feedback to the user, such that the user may be guided to complete scanning a high-quality 3D digital representation of a dental object without a monitor in short time and without overloading the processor with a too high number repetitive surface information data.

Furthermore, the added information may be obtained in many different forms, e.g. in one embodiment it may be a matrix representing different parameters, such as the mentioned geometry, color, and/or diagnostic information and in other embodiments the added information may be represented by a single numerical value. This numerical value may additionally be normalized such that a number between 0-1 will represent the amount of added information. In one example, the added information may result from the comparison between one or more digital 3D representation(s).

More specifically, the added information may result from the comparison of a new scan data with at least one of the existing digital 3D representation(s). The comparison may include any difference between the new scan data and the at least one of the existing digital 3D representation(s) such as an expansion of an existing surface information of the at least one of the existing digital 3D representation(s). As described in FIG. 2A-D and especially in FIG. 2B and FIG. 2C, the expansion of the existing surface of the at least one of the existing digital 3D representation(s) is represented. This expansion of the existing surface can constitute a difference between at least one of the digital 3D representations with the new scan data of the dental object, such as a tooth (200), as shown in FIG. 2A-D. Thus, the 3D scanner system may be configured to provide a feedback signal that correlates with the expansion of the 3D surface of the existing digital 3D representation. In some embodiments, a first feedback signal is correlated with the expansion of the surface, and a second feedback signal is correlated with the removal of an overlay present on the digital 3D representation. In some cases, the two feedback signals are both auditory signals, wherein e.g. the volume or pitch is different among the two signals. The overlay may indicate areas on the representation of inferior quality that are preferably re-scanned.

In some embodiments of the computer-implemented method, the step of determining added information comprises the steps of:

- determining the surface area of the digital 3D representation;
- fusing the new scan data to the digital 3D representation to generate an updated digital 3D representation;
- determining the surface area of the updated digital 3D representation;
- determining the difference in surface area between the updated and the non-updated digital 3D representation; and
- altering at least a property of the feedback signal based on the determined difference in surface area.

Furthermore, in such embodiments, wherein a difference in surface area is determined, the feedback signal may be an auditory signal comprising a plurality of sound pulses separated by a time delay, wherein the time delay is changed based on the determined difference in surface area. Furthermore, the time delay may be increased when the determined difference in surface area is below a predefined lower threshold, and wherein the time delay is decreased when the determined difference in surface area is above a predefined upper threshold. The time delay may be selected from a predefined first range when the determined difference in surface area is above a predefined upper threshold, and the time delay may be selected from a predefined second range when the determined difference in surface area is below a predefined lower threshold. Preferably, the low end of the predefined second range is above the low end of the predefined first range, wherein the predefined first range covers the range 10 ms to 150 ms, such as 30 ms to 110 ms, and wherein the predefined second range covers the range 50 ms to 250 ms, such as 70 ms to 150 ms. Thus, the processing unit(s) of the 3D scanner system may be configured for determining a surface area of the digital 3D representation and the updated digital 3D representation, and the difference in surface area between said 3D representations may further be determined. In some embodiments, the feedback signal is correlated with the difference in surface area, such that the signal is correlated with how much the surface area of the digital three-dimensional has expanded after the step of updating the digital 3D representation.

In one embodiment, the added information may be evaluated based on surface information from the scan data. At least the new surface information obtained via the new scan data may be added to the digital 3D representation by registering the new surface information to existing surface information of the digital 3D representation to find correspondences such that the new surface information can be registered to the correct location on the digital 3D representation. Upon registration of a new scan data patch, the digital 3D representation may be updated by applying some information from the new scan data to the digital 3D representation.

In one example, the digital 3D representation may be represented as volumetric representation, which may contain voxels. Such a representation in known as a "Signed Distance Field" representation. Each voxel in the volumetric representation may be assigned at least one weight as a measure of data quality which can be used to define a surface, represent a color or any other property associated with the dental object being scanned. The weight of a voxel may be updated when a registered scan data patch provide data associated with that particular voxel, this process is generally referred to as "fusion" in the field of model reconstruction. Scan data received from the scanning device may additionally contain one or more weights associated with the scan data quality. A scan data weight may be based on surface information quality determined from the factors associated with depth map generation additionally a scan data weight may be based on texture quality information determined from factors associated with color acquisition like, angle between scanner and surface information, sensor saturation etc. There may be a scan data weight associated with each individual data element.

When a registered scan data patch is added to the 3D digital representation, the individual weights from the scan data may be added to the corresponding weights in each voxel of the digital 3D representation. Added information may thus be evaluated based on changes in individual or grouped voxels of the digital 3D representation when a new scan data patch is added. If the weight of one or more voxels of the digital 3D representation changes significantly, added data may be determined. By evaluating the change of individual weights one numerical value may be generated representing the extent of added information. Consequently, the feedback signal may be adjusted based on the determined added data or based on the numerical value.

In another example, a new scan data may be registered to its corresponding position to at least one previous scan data.

By using the surface information associated with the individual scan data, a center of mass may be computed for each scan data patch. When a new scan data patch is registered to any previous scan data patches, the distances between the center-of-mass for the closest previous scan patches may be used to evaluate the added information as a measure of overlap between the scan patches. Threshold values may be defined, such that a distance between the center-of-mass of the new scan data to the closest corresponding precious scan data below a minimum threshold is equal to complete overlap and if a distance above a maximum threshold value equals maximum expansion of the surface information.

The possible difference between at least one of the existing digital 3D representation(s) with the new scan data of the dental object may be described by an update of data in an existing surface of the at least one of the digital 3D representation(s). This update of data can be a difference in color, fluorescence and/or texture of the dental object being scanned.

FIG. 2A-D show some schematic views of an embodiment of a dental object, more specifically a tooth (200), with an example of an expansion of surface and/or an update of data in at least one of the digital 3D representations. These figures illustrate different scenarios that may happen when a user scans a dental object with an intraoral scanning device, which is shown in FIG. 2A-D as a handheld intraoral scanning device (206).

Figure 2A:
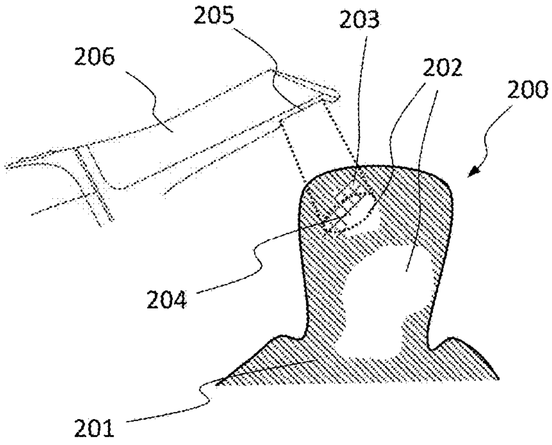
FIG. 2A-D show schematic views of an embodiment of a dental object with an example of an expansion of surface and/or an update of data in at least one of the digital 3D representations.

FIG. 2A shows a schematic view of an embodiment of a dental object, more specifically a tooth (200), where a handheld intraoral scanning device (206) is scanning an area (204) comprising a partially scanned area (203) and a non-scanned area (202).

The scanning area (204) of the handheld intraoral scanning device (206) may also cover a part of the scanned area (201). As can be seen in FIG. 2A (and also 2B-D) the scanning area (204) may cover smaller or larger part(s) of the scanned area (201) which may affect the provided feedback signal. In some embodiments, where the scan areas (204), such as scan patches or subscans, are stitched together, the scanning area (204) may have to cover at least a minor part of the previous scanned area (201) in order to determine common features allowing for the stitching process to be successful.

The partially scanned area (203) defines an area where some scan data has been previously scanned, but where some additional scan data are either missing, insufficient or with low quality, such as surface, color, texture information, shade measurement, and/or diagnostic data. The scanning scenario described in FIG. 2A may create a combination of two possible added information previously described, i.e. an expansion of an existing surface, where the scanner (206) receives new data from the non-scanned area (202) and an update of data in the existing surface, where the scanner (206) receives additional data from the partially scanned area (203).

Accordingly, at least two types of added information may be determined, one for the information received from non-scanned area (202) and another for the partially scanned area (203). The added information may in another embodiment be considered as the cumulative of the two, or in yet a further embodiment as an average.

Similarly, the feedback signal may be provided by using both types of added information or the added information with the highest content of relevant added information determined when comparing the new scan data, e.g. data received from either non-scanned area (202) and/or from the partially scanned area (203), with the digital 3D representation, such as the tooth scan (201).

Figure 2B:
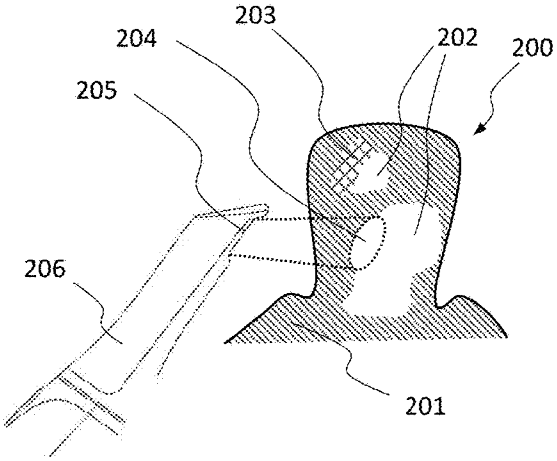

FIG. 2B shows a schematic view of an embodiment of a dental object, more specifically a tooth (200), where a handheld intraoral scanning device (206) obtains scan data from a scanning area (204). As can be seen, the field of view (204) of the handheld intraoral scanning device (206) substantially covers an area of the dental object which has not been scanned before, namely a non-scanned area (202). This scanning scenario potentially provides more added information to the digital 3D representation of the dental object compared to the embodiment disclosed above where the non-scanned area (202) is relative smaller. Accordingly, if the added information considered relates to added scan data in the 3D representation, a feedback signal may be provided as an output to a user, which will inform the user that a lot of relevant information is received and the scanning process is proceeding well. In one embodiment where the added information may be characterized by a single numerical value in a range describing the amount of added information received, it may be expected that this numerical value would be close to its maximum value, e.g. in the high end of the range.

Figure 2C:
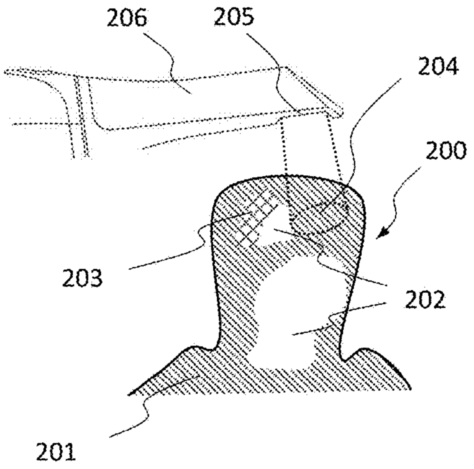

FIG. 2C shows a schematic view of an embodiment of a dental object, more specifically a tooth (200), where the handheld intraoral scanning device (206) obtains scan data from a scanning area (204). As can be seen, the field of view (204) of the handheld intraoral scanning device (206) substantially covers an area of the dental object which has been scanned before, namely a scanned area (201). This scanning scenario potentially provides relative low amount of added information to the digital 3D representation of the dental object since the scanning area (204) already is of high quality in that area of the existing digital 3D representation of the dental object. A high-quality area may refer to an area covered by scan data obtained from multiple angles through several overlapping scan patches. Comparing this to the embodiment described with respect to FIG. 2B where the added information may be described using a numerical value, it may be expected that this numerical value would be close to its minimum value, e.g. in the low end of the range.

Figure 2D:
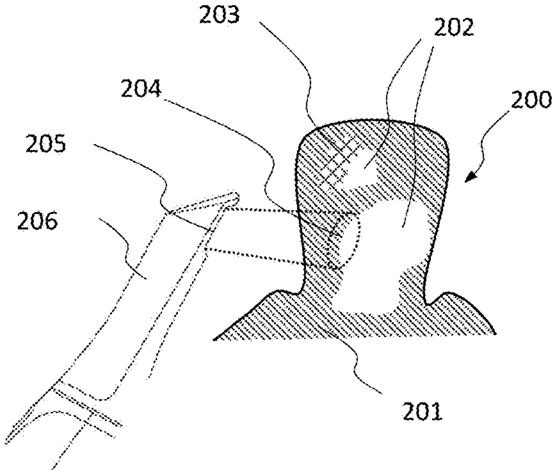

FIG. 2D shows a schematic view of an embodiment of a dental object, more specifically a tooth (200), where the handheld intraoral scanning device (206) obtains scan data from a scanning area (204). As can be seen, the field of view (204) of the handheld intraoral scanning device (206) substantially overlaps an area of the dental object which has been scanned before and simultaneously covers an area of the dental object which has not been scanned before. This scanning scenario provides a relatively high added information to the digital 3D representation of the dental object since the scanning area (204) is comprising an area which has not been scanned before. At the same time, the scanning area (204) also comprises an area which has been scanned before. Comparing this to the embodiment discussed with respect to FIGS. 2B and C above where the added information is described using a numerical value, it may be expected that it would be set to a numerical value in the middle of the range that describes the amount of added information.

In some embodiments, the added information is characterized by a numerical value, for example as discussed briefly with respect to FIGS. 2B-2D. The numerical value may vary depending on the added information. The generated feedback signal can be based on the numerical value. The numerical value can for example be a value determined within a pre-set range or may be normalized such that the range of values may be 0-1. For instance, if the numerical value becomes relatively high, for example when it is close to the high end of the pre-set range, then the feedback signal may be generated with some special characteristics and/or settings. If the numerical value becomes relatively low, for example when it is close to the low end of the pre-set range, then the feedback signal may be generated with some other special characteristics and/or settings. This concept will be described in more details in the next paragraphs with specific applications.

The feedback signal may be provided as a digital signal or an analogue signal. An analogue signal may be any continuous signal representing some other quantity to another quantity. For instance, in an analogue audio signal, the instantaneous signal voltage varies continuously with the pressure of the sound waves. In the case of the present disclosure, an analogue signal can be implemented as the feedback signal by continuously providing a feedback which may correlate to the added information. Preferably, a digital signal can be implemented as the feedback signal. The digital signal may be adapted to be sent to at least one output device. The at least one output device may be an audio device and/or a haptic device and/or a light-emitting device, or any combination of these three device types.

For instance, an audio device can provide an audible signal output while a haptic feedback may deliver a haptic output, e.g. rumbling, based on the feedback signal, to the user. The feedback signal may be configured differently depending on the type of feedback provided. For examples, a pattern of pulses may be used for haptic, audio and visual feedback, however, the amplitude and frequency may vary. As an example, the temporal distance between the pulses may be adjusted such that the frequency is increased or decreased, wherein the adjustment is correlated to the rate of new scan data acquired. In particular, the temporal distance may be decreased when the rate is high, corresponding to imaging new areas of the dental object, wherein the scan data has a relatively small overlap with the existing 3D representation. Similarly, the temporal distance may be increased when the rate is low, corresponding to imaging areas of the dental object, which largely already form part of the 3D representation, wherein the scan data has a relatively high overlap with the existing 3D representation.

In some embodiments multiple feedback signals may be generated, e.g. a first feedback signal adapted to be sent to an audio device, a second feedback signal adapted to be sent to a light-emitting device and/or a third feedback signal adapted to be sent to a haptic output device. Accordingly, the user may be prompted in different ways on where to scan.

Figure 3A:
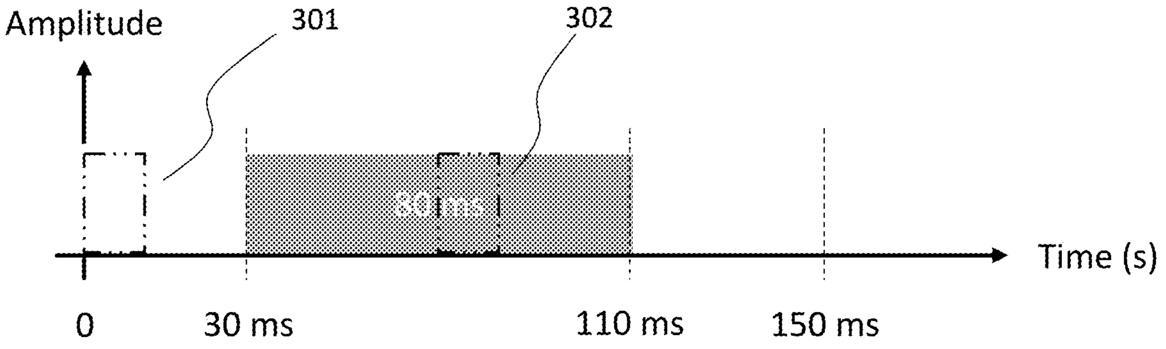
FIG. 3A-B show a description of the feedback signal properties when it is adapted to be output to an audio device.
Figure 3B:
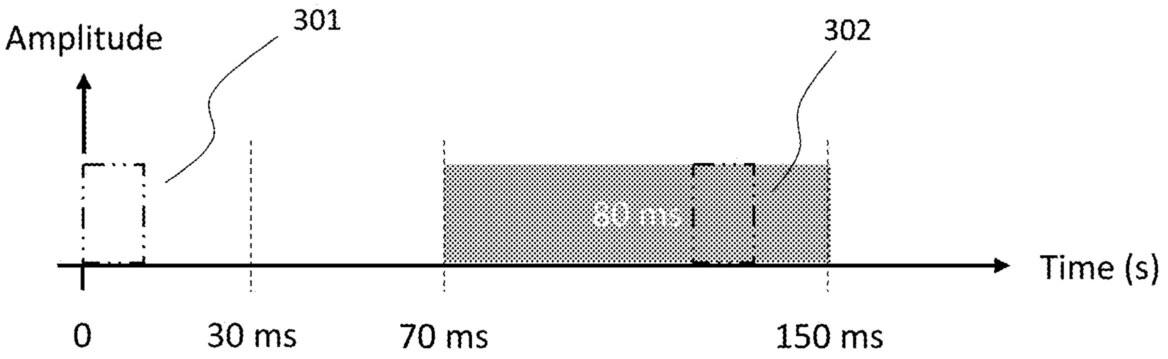

Accordingly, one embodiment of a digital signal being adapted/configured to be sent to an audio device is disclosed, where the digital signal may be modulated based on the added information. FIG. 3A-B show a description of the digital signal properties when it is adapted to be outputted to an audio device. As it is described on FIG. 3A-B, the digital signal may comprise a plurality of successive pulses, wherein each pulse can be separated by a variable time delay. Preferably, the individual pulse width may be shorter than the variable time delay, especially in order to allow a following pulse (302) not to be covered by a previous pulse (301). The variable time delay may be between 10 ms to 300 ms, preferably between 20 ms to 200 ms, even more preferably between 30 ms to 150 ms. The variable time delay may vary based on the numerical value. As described previously, the feedback signal can vary based on the numerical value.

FIG. 3A shows a range of suitable time delays between two successive pulses, wherein time delays selected in said range correspond to a 'short' time delay. The time delay between two pulses in this regime is preferably between 30 ms to 80 ms. FIG. 3A shows a description of the digital signal property when it is adapted to be outputted to an audio device when the added information is relatively high. FIG. 3B shows a range of suitable time delays between two successive pulses, wherein time delays selected in said range correspond to a 'long' time delay. The time delay between two pulses in this regime is preferably between 70 ms to 150 ms FIG. 3B shows a description of the digital signal property when it is adapted to be outputted to an audio device when the added information is relatively low. The sound that would be generated based on these specific settings makes the user easily understand that a new area with added information is being scanned. It has an analogy with a vacuum cleaner where there is noise generated by the vacuum cleaner, especially in the pipe where dust or small particles are vacuumed. Indeed, when more dust is vacuumed, the noise generated by the pipe of the vacuum cleaner has an analogy with a digital audio signal comprising successive pulses being closer and closer in time. This gives a good indication to the user that something new may occur in the process of scanning and the analogy to the well-known process of vacuum cleaning gives the user a satisfying experience when pulses are close to each other which gives a feeling of collecting and vacuuming a lot of added information.

In another embodiment, the digital signal can be defined by different pitches that may correlate to the added information. The pitch is a perceptual property of sounds that allows their ordering on a frequency-related scale, or more commonly, pitch is the quality that makes it possible to judge sounds as "higher" or "lower" in the sense associated with musical melodies. In order to be audible, a generated sound may have its frequency comprised between 20 Hz to 20 kHz. In this specific example, the successive pulses can have different pitches, which would create different audible sounds depending on the added information. In other terms, the pitch may be correlated to the added information. In this context, the added information would be characterized by "lower" or "higher" audible sounds, depending on the added information. It may be preferred that "lower" audible sounds can be heard when the added information is relatively low, while "higher" audible sounds can be heard when the added information is relatively high.

The dental object may be an object that can be included in a mouth. More generally, the dental object can be for instance a jaw, more specifically gingiva (gum), floor of mouth, a tooth (200), a group of teeth, an implant or a restoration. The dental object may be an intraoral dental object of a patient, said dental object comprising e.g. teeth and/or gingiva of the patient. Such a dental object may further comprise other objects and/or materials inside the patient's oral cavity, for example implants or dental restorations. The dental object may only be a part of the patient's teeth and/or oral cavity, since the entire set of teeth of the patient is not necessarily scanned during a given scanning session. Examples of dental objects include one or more of: tooth/teeth, dental arch(es), implant(s), dental restoration(s), dental prostheses, edentulous ridge(s), and combinations thereof. Alternatively, the dental object may be a gypsum/plaster model representing a patient's teeth.

The scan data comprises information relating to the three-dimensional dental object. The scan data may comprise any of: 2D images, 3D point clouds, depth data, texture data, diagnostic data, intensity data, color data, 2D IR data and/or combinations thereof. As an example, the scan data may comprise one or more point clouds, wherein each point cloud comprises a set of 3D points describing the three-dimensional dental object. As another example, the scan data may comprise images, each image comprising image data e.g. described by image coordinates and a timestamp (x, y, t), wherein depth information can be inferred from the timestamp. The image sensor(s) of the scanning device may acquire a plurality of raw 2D images of the dental object in response to illuminating said object using the one or more light projectors. The plurality of raw 2D images may also be referred to herein as a stack of 2D images. The 2D images may subsequently be provided as input to the processor, which processes the 2D images to generate scan data. The processing of the 2D images may comprise the step of determining which part of each of the 2D images are in focus in order to deduce/generate depth information from the images. The depth information may be used to generate 3D point clouds comprising a set of 3D points in space, e.g., described by cartesian coordinates (x, y, z). The 3D point clouds may be generated by the processor or by another processing unit. Each 2D/3D point may furthermore comprise a timestamp that indicates when the 2D/3D point was recorded, i.e., from which image in the stack of 2D images the point originates. The timestamp is correlated with the z-coordinate of the 3D points, i.e., the z-coordinate may be inferred from the timestamp. Accordingly, the output of the processor is the scan data, and the scan data may comprise image data and/or depth data, e.g. described by image coordinates and a timestamp (x, y, t) or alternatively described as (x, y, z). The scanning device may be configured to transmit other types of data included in the scan data. Examples of additional data include 3D information, texture information, diagnostic modalities such as infra-red (IR) images for detecting internal structures of the dental object, fluorescence images, reflectance color images, x-ray images, and/or combinations thereof.

The scan data may comprise at least one two-dimensional (2D) image and/or a scan patch. The scan data may comprise any of 2D images, 3D point clouds, depth data, texture data, intensity data, colour data, and/or combinations thereof. As an example, the scan data may comprise one or more point clouds, wherein each point cloud comprises a set of 3D points describing the three-dimensional dental object. A scan patch can be defined as a combination of at least one distance and at least one 2D image. The scan patch can be generated via a scan procedure. A scan procedure may be performed with an optical sensor (205), placed at a given distance from the object to be scanned. Therefore, a combination of a distance from the optical sensor (205) to the object as well as at least one 2D image recorded at an instant may be comprised in the scan patch. The scan procedure can be done with a scanning device, such as an intraoral scanning device, comprising the optical sensor (205), which is operated by projecting a pattern and translating a focus plane along an optical axis of the scanning device and capturing a plurality of 2D images at different focus plane positions such that each series of captured 2D images corresponding to each focus plane forms a stack of 2D images.

More specifically, the focus plane position may be preferably shifted along the optical axis of the scanning system, such that 2D images captured at a number of focus plane positions along the optical axis form said stack of 2D images for a given view of the object, i.e. for a given arrangement of the scanning system relative to the object. This stack of 2D images may also be referred as a sub-scan.

FIG. 4 shows a perspective view of an embodiment of an 3D scanner system (400) for scanning a dental object and which can be used in a computer implemented method for providing feedback during scanning as discussed herein and described in relation to the Figures above. The 3D scanner system (400) can comprise an intraoral scanning device, which may comprise at least one optical sensor (205) for obtaining scan data of preferably a dental object. The 3D scanner system (400) may comprise one or more processing unit(s) which can be configured to perform the steps of:

- generating a digital three-dimensional (3D) representation of the dental object based on current scan data (102);
- obtaining new scan data of the dental object (103);
- generating an updated digital 3D representation by adding the new scan data to the digital 3D representation (104);
- determining added information to the digital 3D representation by comparing the new scan data to at least one of the digital 3D representation(s) and/or by comparing the updated digital 3D representation to the digital 3D representation(s) (105); and
- providing a feedback signal (106), wherein the feedback signal correlates with the added information.

These steps can be continuously performed as previously discussed. As shown in FIG. 4, the 3D scanner system (400) may comprise a desktop or a laptop computer (401) with a screen.

The 3D scanner system may also comprise a scanning device or any other type of devices that can comprise at least one optical sensor (205). FIG. 4 shows an embodiment of an 3D scanner system (400) comprising an intraoral scanning device and a computer. A communication between the desktop or the laptop computer and the scanning device can be a wire-based or wireless communication (404), using wireless standards such as Bluetooth or Wi-Fi. The desktop or laptop computer screen may be used to display the digital 3D representation(s) (402) of the dental object. The at least one optical sensor (205) can preferably be an electro-optical sensor or a photoelectric sensor or a flash detection sensor. More generally, the at least one optical sensor (205) is an electronic detector that convert light, or a change in light, into an electronic signal. It can advantageously be able to detect electromagnetic radiation from the infrared up to the ultraviolet wavelengths.

The 3D scanner system (400) may be a dental scanning system that may include an intraoral scanning device such as the TRIOS series scanners from 3Shape A/S or a laboratory-based scanner such as the E-series scanners from 3Shape A/S.

The intraoral scanning device may comprise one or more light projectors configured to generate an illumination pattern to be projected on a three-dimensional dental object during a scanning session. The light projector(s) preferably comprises a light source, a mask having a spatial pattern, and one or more lenses such as collimation lenses or projection lenses. The light source may be configured to generate light of a single wavelength or a combination of wavelengths (mono- or polychromatic). The combination of wavelengths may be produced by using a light source configured to produce light (such as white light) comprising different wavelengths. Alternatively, the light projector(s) may comprise multiple light sources such as LEDs individually producing light of different wavelengths (such as red, green, and blue) that may be combined to form light comprising the different wavelengths. Thus, the light produced by the light source may be defined by a wavelength defining a specific color, or a range of different wavelengths defining a combination of colors such as white light. In an embodiment, the scanning device comprises a light source configured for exciting fluorescent material of the teeth to obtain fluorescence data from the dental object. Such a light source may be configured to produce a narrow range of wavelengths. In another embodiment, the light from the light source is infrared (IR) light, which is capable of penetrating dental tissue. The light projector(s) may be DLP projectors using a micro mirror array for generating a time varying pattern, or a diffractive optical element (DOF), or back-lit mask projectors, wherein the light source is placed behind a mask having a spatial pattern, whereby the light projected on the surface of the dental object is patterned. The back-lit mask projector may comprise a collimation lens for collimating the light from the light source, said collimation lens being placed between the light source and the mask. The mask may have a checkerboard pattern, such that the generated illumination pattern is a checkerboard pattern. Alternatively, the mask may feature other patterns such as lines or dots, etc.

The scanning device preferably further comprises optical components for directing the light from the light source to the surface of the dental object. The specific arrangement of the optical components depends on whether the scanning device is a focus scanning apparatus, a scanning device using triangulation principle, confocal scanning, depth of defocus, light field, stereoscopic, deep learning based 3D measurements or any other type of scanning device.

In some embodiments, the intraoral scanning device is based on a focus scanning principle, such as depth-from-focus. In such embodiments, the scanner comprises an optical element, such as a focus lens, which is configured to move back and forth during scanning to change the focus of the scanner, whereby the depth can be estimated based on a focus measure. A focus scanner is further described in EP 2 442 720 B1 by the same applicant, which is hereby incorporated herein by reference. In some embodiments, the intraoral scanning device is based on a depth-from-defocus scanning principle, wherein an optical property, such as an aperture, is changed between the acquisition of two images, whereby depth can be estimated by determining the degree of defocus between the two images.

In some embodiments, the intraoral scanning device is based on triangulation, wherein at least one image sensor and a projector unit are positioned such that they form a triangle with respect to a point on the scanned surface. As an example, a projector and an image sensor may be utilized to determine points in 3D space based on triangulation. Alternatively, the intraoral scanning device may comprise two or more image sensors viewing the scene or scanned object from two different directions, wherein the image sensors are configured to acquire a set of images, wherein a correspondence problem is solved based on triangulation. The correspondence problem generally refers to the problem of ascertaining which parts of one image correspond to which parts of another image. Specifically, the projector unit may be configured to project a plurality of projector rays, which are projected onto a surface of the dental object. In particular, solving the correspondence problem may include the steps of determining image features in the images within a set of images, and further associate said image features with a specific projector ray. Subsequently, the depth of each projector ray may be computed, whereby a 3D representation of the scanned object may be generated.

The light reflected from the dental object in response to the illumination of the dental object is directed, using optical components of the scanning device, towards the image sensor(s). The image sensor(s) are configured to generate a plurality of images based on the incoming light received from the illuminated dental object. The image sensor may be a high-speed image sensor such as an image sensor configured for acquiring images with exposures of less than 1/1000 second or frame rates in excess of 250 frames pr. second (fps). As an example, the image sensor may be a rolling shutter (CCD) or global shutter sensor (CMOS). The image sensor(s) may be a monochrome sensor including a color filter array such as a Bayer filter and/or additional filters that may be configured to substantially remove one or more color components from the reflected light and retain only the other non-removed components prior to conversion of the reflected light into an electrical signal. For example, such additional filters may be used to remove a certain part of a white light spectrum, such as a blue component, and retain only red and green components from a signal generated in response to exciting fluorescent material of the teeth.

The 3D scanner system preferably further comprises a processor configured to generate scan data (intraoral scan data) by processing the two-dimensional (2D) images acquired by the scanning device. The processor may be part of the scanning device. As an example, the processor may comprise a Field-programmable gate array (FPGA) and/or an Advanced RISC Machines (ARM) processor located on the scanning device The one or more processing unit(s) may be comprised in the 3D scanner system, wherein the one or more processing unit(s) may be either comprised in the desktop or laptop computer (401) or in the scanning device or any other type of devices that can comprise at least one optical sensor (205). More generally, the scanning device or any other type of devices may comprise a scanner housing which can comprise the one or more processing unit(s).

The 3D scanner system (400) may further comprise at least one output device for providing an output to a user during scanning. The at least one output device can be an audio device and/or a haptic device and/or a light-emitting device. The audio device can be a speaker, which may be wireless or wire-based connected to the intraoral scanning device. The power of the speaker may depend on a specific user need. The speaker may be either comprised in the housing of the intraoral scanning device (400), or can also be an external device. The haptic device is based on the haptic technology, which refers to any technology that can create an experience of touch by applying forces, vibrations, or motions to a user. The haptic device can be any device that may be able to implement a haptic effect to a user. The implementation of a haptic technology can be divided in multiple categories such as vibration, force feedback, air vortex rings or ultrasound. One potential implementation of a feedback signal in the intraoral scanning device can be a vibration effect which may correlate to the added information. The vibration effect may be modulated depending on the added information. The light-emitting device can be any device that can emit light. The light-emitting device may be a light-emitting diode. A light-emitting diode may have the advantage of having a light weight, a good efficiency and an option of emitting different colours in a relatively small area. The light-emitting device can be comprised in the intraoral scanning device, but it may also be a peripheral (auxiliary) device, which may have to be connected to the 3D scanner system in order to get the output based on the feedback signal from the intraoral scanning device. The light-emitting device can be comprised in the intraoral scanning device, wherein the light-emitting device may be comprised in the housing of a handheld intraoral scanning device (206).

A handheld intraoral scanning device (206) may comprise a scanner housing and can be configured to be handled with one hand. The scanner housing may comprise:

an optical sensor (205) for preferably obtaining scan data of a dental object;

one or more processing unit(s) for processing the scan data; and one or more output device(s) for providing an output to a user.

Figure 5:
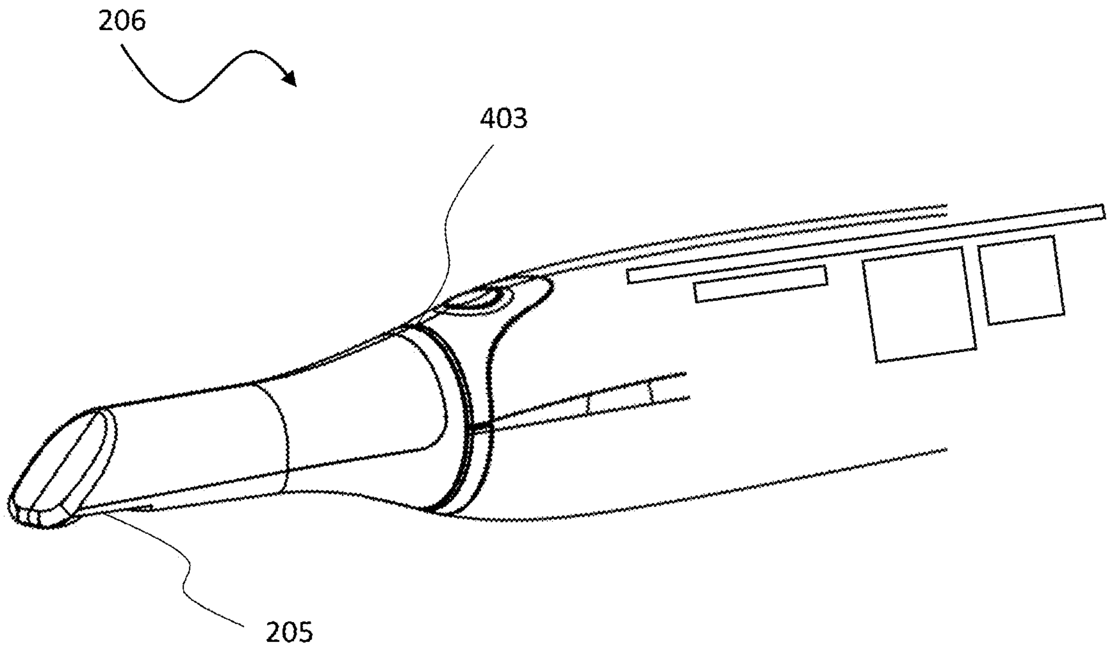
FIG. 5 shows a perspective view of an embodiment of a handheld intraoral scanning device.

FIG. 5 shows a schematic view of an embodiment of the handheld intraoral scanning device (206). The handheld intraoral scanning device (206) comprises an optical sensor (205) and one or more processing unit(s).

The handheld intraoral scanning device (206) may be configured for receiving at least one feedback signal that may be provided by the computer-implemented method (100) previously described. The handheld intraoral scanning device (206) may provide an output to an user from the one or more output device(s) based on the at least one feedback signal.

The one or more processing unit(s) may process the scan data obtained from an optical sensor (205). The one or more processing unit(s) can also output the scan data to a peripheral device, which can then process the scan data, outside from the handheld intraoral scanning device (206). The one or more processing unit(s) may also pre-process the scan data before outputting a pre-processed scan data to a peripheral device. The pre-processed scan data can be any step from a step following the acquisition of the scan data of a dental object until a step of delivering an information to an external screen which can be visualized by a user. More generally, the one or more processing unit(s) being comprised in the handheld intraoral scanning device (206) can perform one, more or all of the steps of the computer-implemented method (100).

The one or more output device(s) of the handheld intraoral scanning device (206) can be at least one audio device and/or at least one light-emitting device and/or at least one haptic device. The one or more output device(s) may be located in the housing of the handheld intraoral scanning device (206) but may also be located on the housing, such as it becomes visible to the user, especially in the potential case of the one or more output device(s) being at least one light-emitting device. FIG. 5 shows a schematic view of an embodiment of the handheld intraoral scanning device (206), with a possible implementation of the one or more output device(s).

In one embodiment, the handheld intraoral scanning device (206) may comprise at least one audio device, the at least one audio device being preferably a speaker. The handheld intraoral scanning device (206) can further comprise a wireless module, which may be able to communicate with at least one audio device being potentially external of the handheld intraoral scanning device (206) housing. The handheld intraoral scanning device (206) may also comprise a jack plug or any other plugs that can allow the handheld intraoral scanning device (206) to be connected to an audio device. The at least one audio device can be configured to output the feedback signal.

In another embodiment, the handheld intraoral scanning device (206) can comprise the at least one light-emitting device. The at least one light-emitting device can be a device comprising at least one LED device. The light-emitting device, such as the at least one LED device, may be configured to output different colours and/or different brightness. This would potentially allow the user to get different information based on the feedback signal. As an example, the brightness of the light-emitting device can be correlated the added information, which means that the brightness may be correlated to the feedback signal. In that specific configuration, the feedback signal can be adapted/pre-processed by either the handheld intraoral scanning device (206) or in the housing of the handheld intraoral scanning device (206), in order to be adapted for being outputted to the light-emitting device.

The light-emitting device may be at least one LED ring (403), as shown in FIG. 5. The at least one LED ring (403) may preferably be located in an area where the manipulation of the handheld intraoral scanning device (206) by the user does not interfere with the at least one LED ring (403). In other terms, the at least one LED ring (403) may be located close to the at least one optical sensor (205), as it is shown in FIG. 5.

Figure 6A:
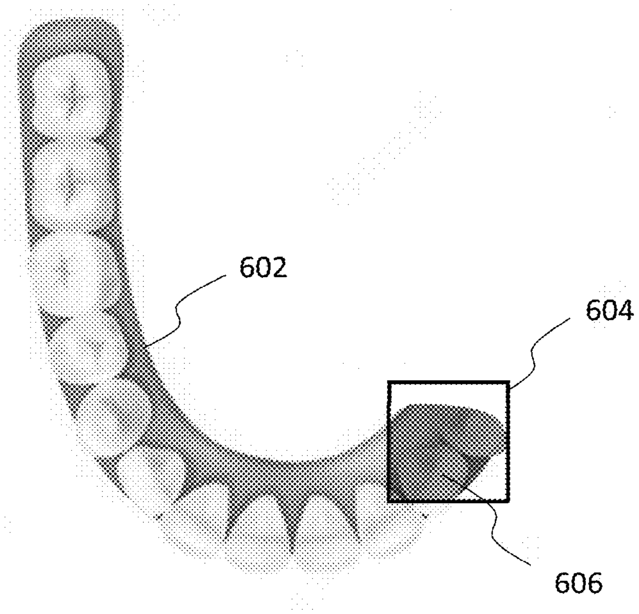
FIG. 6A-B show a rendition of a dental object, here a dental arch, being scanned, wherein a field of view of the scanning device is indicated.
Figure 6B:
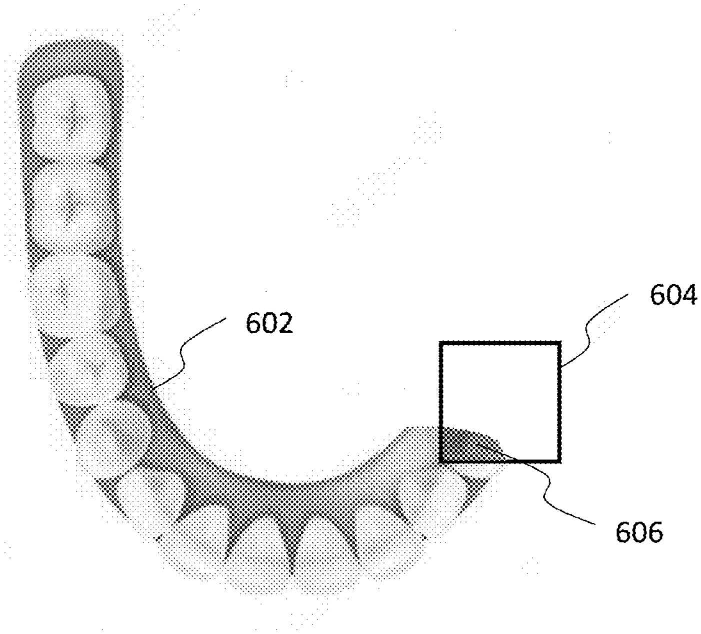

FIG. 6A-6B show a rendition of a dental object (602), here a dental arch, being scanned. Typically, the scanning device is configured for generating the digital 3D representation of the dental object based on a plurality of scan patches, wherein each scan patch comprises 3D scan data or a depth map, such as a point cloud, of a part of the dental object. Thus, the digital 3D representation may be generated by stitching a plurality of said scan patches together to form a representation which is larger than what can be captured in a single field of view of the scanning device. The scanning device typically acquires a fixed amount of 3D scan patches/3D images per unit of time, such as between 20 and 30 scan patches per second. Thus, if the user moves the scanning device slowly across the dental arch, there is typically a large overlap between the existing 3D representation and a given new scan patch corresponding to the given field of view. The large overlap results in excessive amount of 3D scan data, which is computationally heavy to deal with as the 3D representation expands. Thus, it is desired to encourage the user to move the scanning device faster or at least capture new areas of the dental object, which does not already form part of the 3D representation. This can be achieved by providing a feedback signal, such as an auditory or visual feedback signal, that correlates with the amount of overlap between the digital 3D representation and a given new 3D scan patch. In the example of FIG. 6A, this overlap is large; thus, it is desired to have 'long pulses' in the auditory signal corresponding to a long time delay between the pulses. Conversely, in the example of FIG. 6B, the overlap is small; thus, it is desired to have 'short pulses' in the auditory signal corresponding to a short time delay between the pulses. A similar effect can be achieved using a visual feedback signal, e.g. by providing a light emitting device in the intraoral scanning device, wherein the light-emitting device is configured for changing a brightness level of the visual feedback signal based on the determined overlap and/or difference in surface area.

Figure 7:
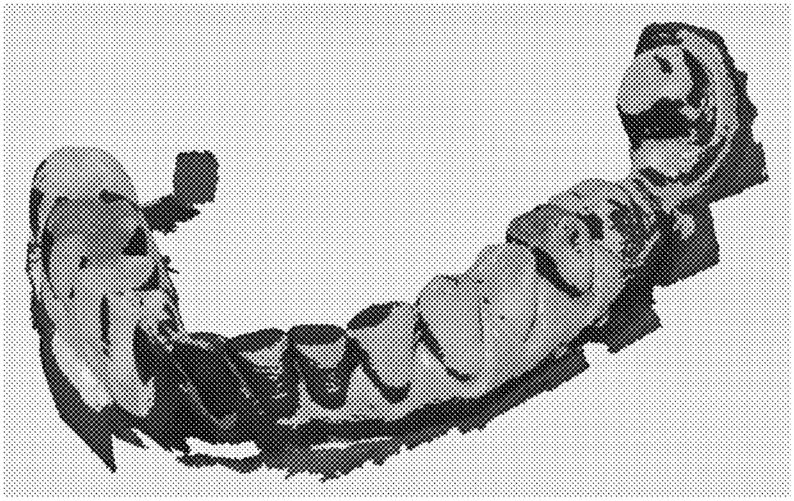
FIG. 7 shows a digital 3D representation of a dental arch, which has been scanned using a scanning device according to the present disclosure.

FIG. 7 shows a digital 3D representation of a dental arch, which has been scanned using an intraoral scanning device. The 3D scanner system may be configured for generating one or more overlays on the digital 3D representation. The 3D representation and the overlay may be shown in a graphical user interface on a display. In this example, an overlay is indicated in the figure as dark grey, wherein the overlay indicates the scan quality e.g. in terms of shade measurement. The scan quality can also be influenced by other scan modalities such as a fluorescence imaging modality or an infrared imaging modality. In some embodiments, the overlay indicates areas of low scan quality, thus encouraging the user to re-scan said areas. Thus, the 3D scanner system may be configured such that the user can re-scan the dental arch; in particular, the system may be configured for updating the overlay based on said re-scan, such that part(s) of the overlay may be removed after re-scanning the dental arch and obtaining a better scan quality of the digital 3D representation. In some cases, the 3D scanner system is configured to provide a feedback signal that correlates with the removal of the overlay. This feedback signal may be any of the feedback signals disclosed herein, and it may be modulated in any of the ways described herein. In some embodiments, the 3D scanner system is configured for removing, in real-time, part(s) of the overlay that are re-scanned by the user, such that a visual feedback is immediately provided to the user. Additionally, the scanner system may provide an auditory feedback signal correlated to the removal of the overlay, such that the user is given multiple forms of feedback in relation to said removal.

Figure 8:
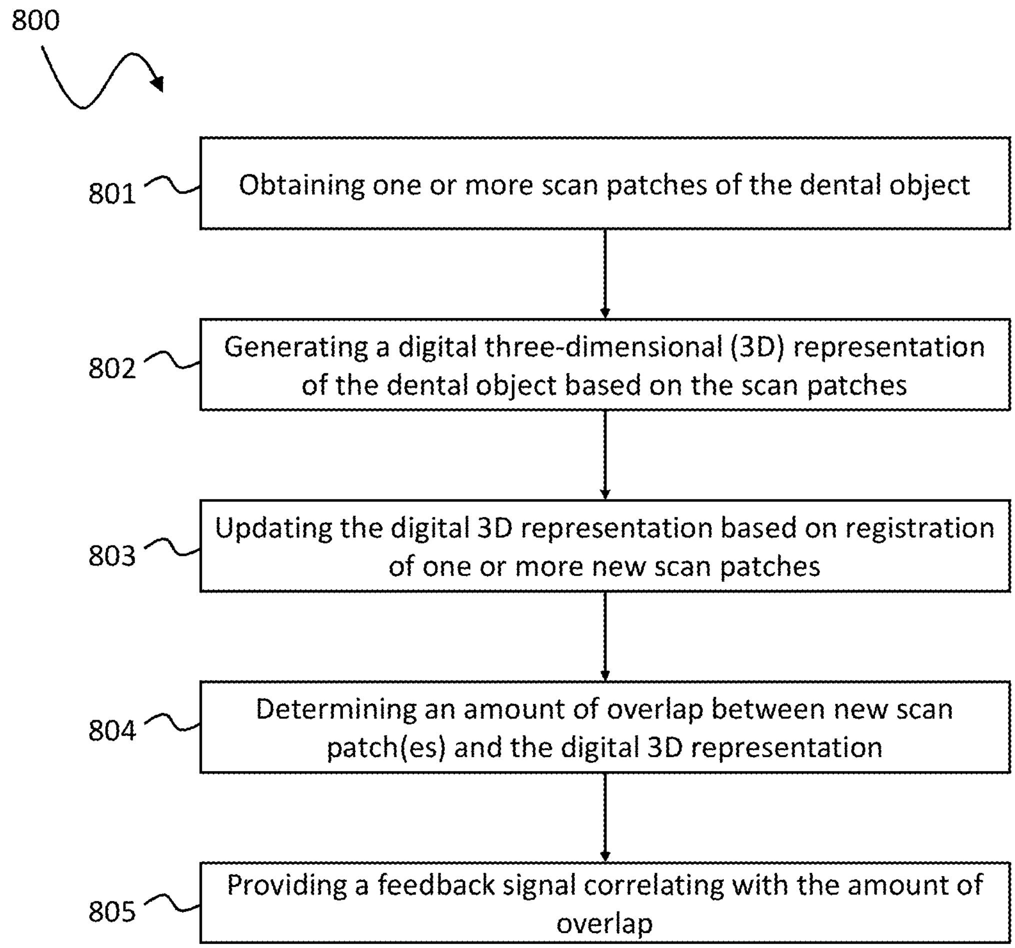
FIG. 8 shows a flow-chart of an embodiment of the computer-implemented method according to the present disclosure.

FIG. 8 shows a flow-chart (800) of an embodiment of the computer-implemented method according to the present disclosure. In this embodiment, the method comprises the steps of obtaining one or more scan patches of the dental object (step 801), generating a digital three-dimensional (3D) representation of the dental object based on the scan patches (step 802), updating the digital 3D representation based on registration of one or more new scan patches (step 803), determining an amount of overlap between new scan patch(es) and the digital 3D representation (step 804), and providing a feedback signal correlating with the amount of overlap (step 805).

In some embodiments, the scanning device comprises a beam splitter. A beam splitter may be understood as an optical device configured to split a beam of light in two beams. The beam splitter may be made from two triangular glass prisms which are attached together at their base. The face where the two triangular glass prisms are attached may form an interface, where incident light may be transmitted and/or reflected. The interface may be coated with a coating. The coating may be configured to allow light within a certain range of wavelengths of a certain polarization to pass. Thus, the beam splitter may be configured to accept light of a certain range of wavelengths, e.g. being unpolarized, and then output/transmit light of the same wavelengths of linear polarization.

The beam splitter may be configured such that the polarization of two exiting beams from the beam splitter are orthogonal to each other, e.g. one beam of horizontally linearly polarized light and another beam of vertically linearly polarized light. Thus, the beam splitter may be a polarizing beam splitter. The beam splitter may be configured to receive an incident beam of light and output two beams of light, wherein at least one of said beams is linearly polarized. Thus, the beam splitter may be configured to receive unpolarized light and output linearly polarized light of two different orientations. The beam splitter may be a beam splitter cube comprising six square faces. The inside of the beam splitter cube may comprise an interface where the two triangular glass prisms are attached together. Preferably, the beam splitter is configured to transmit linearly polarized light of a first orientation, e.g. vertical, and further configured to reflect linearly polarized light of a second orientation, e.g. horizontal. The light projected towards the distal end of the scanning device may be linearly polarized of a first orientation, whereas light returning from the object throughout the optical system may be linearly polarized of a second orientation, wherein the beam splitter is configured to reflect the light of the second orientation onto the image sensor(s) of the scanning device.

Techniques consistent with the present disclosure provide, among other features, systems and methods for generating a digital three-dimensional representation of a dental object during scanning with an intraoral scanning device and providing feedback during scanning of said dental object. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope. Although operations can be described as a sequential process, some of the operations can in fact be performed in parallel, concurrently, and/or in a distributed environment, and with program code stored locally or remotely for access by single or multi-processor machines. In addition, in some embodiments the order of operations can be rearranged without departing from the spirit of the disclosed subject matter. It will be appreciated by those skilled in the art that the present disclosure can be embodied in other specific forms without departing from the spirit or essential characteristics thereof. The presently disclosed embodiments are therefore considered in all respects to be illustrative and not restrictive. The scope of the disclosure is indicated by the appended claims rather than the foregoing description, and all changes that come within the meaning, range, and equivalence thereof are intended to be embraced therein.

LIST OF ELEMENTS IN FIGURES

100—computer-implement method
101—obtaining current scan data of the dental object
102—generating a digital three-dimensional (3D) representation of the dental object based on the current scan data
103—obtaining new scan data of the dental object
104—generating an updated digital 3D representation by adding the new scan data to the digital 3D representation
105—determining added information to the digital 3D representation by comparing the new scan data to at least one of the digital 3D representation(s) and/or by comparing the updated digital 3D representation to the digital 3D representation(s)
106—providing a feedback signal
200—tooth
201—scanned area
202—non-scanned area
203—partially scanned area
204—scanning area
205—optical sensor
206—handheld intraoral scanning device
301—previous pulse
302—following pulse
400—3D scanner system
401—desktop or laptop computer
402—digital 3D representation
403—LED ring
404—wire-based or wireless communication
602—dental object
604—field of view of scanning device
606—overlap

FURTHER DETAILS OF THE INVENTION

1. A computer-implemented method for providing feedback during scanning of a dental object, comprising the steps of:
obtaining scan data of the dental object;

generating a digital three-dimensional (3D) representation of the dental object based on the scan data;

obtaining new scan data of the dental object;

updating the digital 3D representation based on the new scan data;

determining added information to the digital 3D representation by comparing the new scan data to the digital 3D representation and/or by comparing the updated digital 3D representation to the digital 3D representation; and providing a feedback signal, wherein the feedback signal correlates with the added information and/or correlates with an amount of overlap between the new scan data and the digital three-dimensional (3D) representation.

2. The computer-implemented method according to item 1, wherein the steps are performed continuously and in real-time.

3. The computer-implemented method according to any of the preceding items, wherein the step of updating the digital 3D representation comprises registering the new scan data to the digital 3D representation.

4. The computer-implemented method according to any of the preceding items, wherein the step of determining added information comprises comparing the new scan data to the digital 3D representation, wherein said comparison comprises determining an overlap between the new scan data and the digital 3D representation.

5. The computer-implemented method according to item 4, wherein at least a property of the feedback signal is altered based on the determined overlap.

6. The computer-implemented method according to item 5, wherein the altered property of the feedback signal is selected from the group of: frequency, amplitude, pitch, time delay between pulses of the signal, and/or combinations thereof.

7. The computer-implemented method according to any of the preceding items, wherein the feedback signal is an auditory signal comprising a plurality of sound pulses separated by a time delay, wherein the time delay is changed based on the determined overlap.

8. The computer-implemented method according to item 7, wherein the time delay is decreased when the determined overlap is below a predefined lower threshold, and wherein the time delay is increased when the determined overlap is above a predefined upper threshold.

9. The computer-implemented method according to any of the items 7-8, wherein the time delay is between 10 ms to 300 ms.

10. The computer-implemented method according to any of the items 7-9, wherein the time delay is between 30 ms to 150 ms.

11. The computer-implemented method according to any of the items 7-10, wherein the time delay is selected from a predefined first range when the determined overlap is below a predefined upper threshold, and wherein the time delay is selected from a predefined second range when the determined overlap is above a predefined lower threshold.

12. The computer-implemented method according to item 11, wherein the low end of the predefined second range is above the low end of the predefined first range.

13. The computer-implemented method according to any of the items 11-12, wherein the predefined first range covers the range 10 ms to 150 ms, and wherein the predefined second range covers the range 50 ms to 250 ms.

14. The computer-implemented method according to any of the items 11-1312, wherein the predefined first range covers the range 30 ms to 110 ms, and wherein the predefined second range covers the range 70 ms to 150 ms.

15. The computer-implemented method according to any of the preceding items, wherein the step of determining added information comprises the steps of:

determining the surface area of the digital 3D representation;

fusing the new scan data to the digital 3D representation to generate an updated digital 3D representation;

determining the surface area of the updated digital 3D representation;

determining the difference in surface area between the updated and the non-updated digital 3D representation; and altering at least a property of the feedback signal based on the determined difference in surface area.

16. The computer-implemented method according to any of the preceding items, wherein the feedback signal correlates with the removal of an overlay present on the digital 3D representation.

17. A 3D scanner system for scanning a dental object, wherein the scanner system comprises:

an intraoral scanning device; and one or more processing unit(s) configured to carry out the method according to any of the items 1-15.

18. The 3D scanner system according to item 16, wherein the intraoral scanning device comprises a haptic device configured for providing a haptic feedback signal.

19. The 3D scanner system according to item 18, wherein at least a property of the haptic feedback signal is altered based on the added information and/or the determined overlap.

20. The 3D scanner system according to any of the items 18-19, wherein a vibration level is increased when the determined overlap is below a predefined lower threshold, and wherein the vibration level is decreased when the determined overlap is above a predefined upper threshold.

21. The 3D scanner system according to any of the items 16-20, wherein the intraoral scanning device comprises a light-emitting device configured for providing a visual feedback signal.

22. The 3D scanner system according to item 21, wherein the light-emitting device is configured to change the brightness level of light emitted by the light-emitting device, wherein said brightness level is correlated to the added information and/or the determined overlap.

23. The 3D scanner system according to any of the items 21-22, wherein the light-emitting device is an LED ring located on the intraoral scanning device.

24. The 3D scanner system according to any of the items 17-23, wherein the feedback signal correlates with the removal of an overlay present on the digital 3D representation.

25. A computer-implemented method for providing feedback during scanning of a dental object, comprising the steps of:

obtaining current scan data of the dental object;

generating a digital three-dimensional (3D) representation of the dental object based on the current scan data;

obtaining new scan data of the dental object;

generating an updated digital 3D representation by adding the new scan data to the digital 3D representation;

determining added information to the digital 3D representation by comparing the new scan data to at least one of the digital 3D representation(s) and/or by comparing the updated digital 3D representation to the digital 3D representation(s); and providing a feedback signal;

wherein the feedback signal correlates with the added information.

26. A computer-implemented method for providing feedback to the user during scanning of a dental object using a handheld intraoral scanning device, comprising the steps of:

obtaining current scan data of the dental object;

generating in real time a digital three-dimensional (3D) representation of the dental object based on the current scan data;

providing a non-visible feedback signal to the user;

wherein the non-visible feedback signal is based on the generation of the 3D representation.

obtaining new scan data of the dental object;

generating in real time an updated digital 3D representation by adding the new scan data to the digital 3D representation;

determining added information provided by the new scan data based on the digital 3D representations and/or the scan data; and providing an altered non-visible feedback signal;

wherein the altered feedback signal correlates with the added information.

27. A computer-implemented method for providing feedback during scanning of a dental object using an intraoral scanning device, the method comprising the steps of:

generating first scan data based on images obtained of the dental object;

generating a first 3D representation based on the first scan data;

generating second scan data based on images obtained of the dental object;

generating a second 3D representation based on the second scan data;

determining added data acquired by comparing scan data associated with the first and second 3D representation or by comparing the second scan data to the first 3D representation or by comparing the first and second scan data;

providing a feedback signal in real-time, wherein the feedback signal changes based on the amount of added data.

28. A computer-implemented method for providing feedback during scanning of a dental object using an intraoral scanning device, the method comprising the steps of:

generating a first 3D representation based on first scan data;

generating a second 3D representation based on second scan data;

determining added data acquired by comparing scan data associated with the first and second 3D representation;

providing a feedback signal in real-time, wherein the feedback signal changes based on the amount of added data.

29. A computer-implemented method for providing feedback during scanning of a dental object, the method comprising the steps of:

obtaining scan data using an intraoral scanning device;

updating a 3D representation based on the scan data;

determining added data associated with updating the 3D representation;

providing a feedback signal in real-time, wherein the feedback signal changes based on the amount of added data.

30. The computer-implemented method according to any of the preceding items, wherein one or more of the steps are continuously performed.

31. The computer-implemented method according to any of the preceding items, wherein one or more of the steps are performed continuously and/or in real-time.

32. The computer-implemented method according to any of the preceding items, wherein all steps are performed continuously and in real-time.

33. The computer-implemented method according to any of the preceding items, wherein the added information results in an expansion of an existing surface of at least one of the digital 3D representations.

34. The computer-implemented method according to item 33, wherein the expansion of an existing surface is defined by a difference between at least one of the digital 3D representations with the new scan data of the dental object.

35. The computer-implemented method according to any of the preceding items, wherein the added information describes an update of data in an existing surface of the at least one of the digital 3D representation(s).

36. The computer-implemented method according to any of the preceding items, wherein the added information to the digital 3D representation is characterized by a numerical value.

37. The computer-implemented method according to any of the preceding items, wherein the feedback signal is based on the numerical value.

38. The computer-implemented method according to any of the preceding items, wherein the feedback signal is selected from the group of: auditory, tactile, visual, and/or combinations thereof.

39. The computer-implemented method according to any of the preceding items, wherein the feedback signal is an auditory signal.

40. The computer-implemented method according to item 39, wherein the auditory signal comprises a plurality of sound pulses separated by a distance, wherein the distance shortens when the amount of added data increases.

41. The computer-implemented method according to item 40, wherein the distance lengthens when the amount of added data decreases.

42. The computer-implemented method according to any of the items 39-41, wherein the pitch of the auditory signal is altered based on the amount of added data.

43. The computer-implemented method according to item 42, wherein the pitch is increased when the amount of added data increases, and wherein the pitch is decreased when the amount of added data increases.

44. The computer-implemented method according to any of the preceding items, wherein the feedback signal is a tactile signal, such as a vibration.

45. The computer-implemented method according to any of the preceding items, wherein the feedback signal is outputted by at least one output device.

46. The computer-implemented method according to item 45, wherein the at least one output device is an audio device and/or a haptic device and/or a light-emitting device.

47. The computer-implemented method according to any of the items 45-46, wherein the feedback signal comprises a plurality successive pulses, each pulse being separated by a variable time delay, and wherein each pulse has a pulse width shorter than the variable time delay.

48. The computer-implemented method according to item 47, wherein the variable time delay is between 10 ms to 300 ms, preferably between 20 ms to 200 ms, even more preferably between 30 ms to 150 ms.

49. The computer-implemented method according to items 47-48, wherein the pulse is randomly generated within a time period of 80 ms after the variable time delay.

50. The computer-implemented method according to any of the preceding items, wherein the variable time delay varies based on the numerical value.

51. The computer-implemented method according to any of the preceding items, wherein the feedback signal defines different pitches correlated to the added information.

52. The computer-implemented method according to any of the preceding items, wherein the dental object is a jaw, a tooth, an implant, a restoration, and/or combinations thereof.

53. The computer-implemented method according to any of the preceding items, wherein the scan data can be at least one two-dimensional (2D) image and/or a scan patch.

54. The computer-implemented method according to item 53, wherein a scan patch is a collection of at least one distance and at least one 2D image.

55. The computer-implemented method according to any of the preceding items, wherein the scan data comprises any of image data, geometry data, colour data, fluorescence data, infrared data, and/or combinations thereof.

56. The computer-implemented method according to any of the preceding items, wherein the feedback signal correlates with the removal of an overlay present on the digital 3D representation.

57. A 3D scanner system for scanning a dental object, comprising:
   an intraoral scanning device, comprising at least one optical sensor for obtaining scan data of the dental object;
   a display, and
   one or more processing unit(s) configured to continuously performing the steps of:
      generating a digital three-dimensional (3D) representation of the dental object based on current scan data;
      obtaining new scan data of the dental object;
      generating an updated digital 3D representation by adding the new scan data to the digital 3D representation;
      determining added information to the digital 3D representation by comparing the new scan data to at least one of the digital 3D representation(s) and/or by comparing the updated digital 3D representation to the digital 3D representation(s);
      optionally displaying in real time to the user the updated digital 3D representation; and
      providing a feedback signal, wherein the feedback signal correlates with the added information;
   wherein the 3D scanner system further comprises at least one output device for providing an output to a user during scanning, where the output is based on the feedback signal.

58. The 3D scanner system according to item 57, wherein the one or more processing unit(s) and the intra oral scanner are configured to perform the computer-implemented method according to any one of items 1-55.

59. The 3D scanner system according to item 57 or 58, further comprises that the intra oral scanner is a handheld scanning device comprising a housing containing the at least one optical sensor.

60. The 3D scanner system according to item 59, wherein the housing further contains at least one processing unit.

61. The 3D scanner system according to any one of items 57-60, wherein the scanner system further comprises a desktop or laptop computer comprising a processing unit.

62. The 3D scanner system according to any one of items 57-61, wherein the output device is an audio device and/or a haptic device and/or a light-emitting device.

63. The 3D scanner system according to any of the items 57-62, wherein the feedback signal correlates with the removal of an overlay present on the digital 3D representation.

64. A handheld intraoral scanning device, comprising a scanner housing configured to be handled with one hand, wherein the scanner housing comprises:
   an optical sensor for obtaining scan data of a dental object;
   one or more processing unit(s) for processing the scan data; and
   one or more output device(s) for providing an output to a user;
   wherein the handheld intraoral scanning device is configured for receiving at least one feedback signal provided by a computer-implemented method according to any one of the items 1-55 and providing the output to the user from the one or more output device(s) based on the at least one feedback signal.

65. A handheld intraoral scanning device according to item 64, wherein the one or more processing unit(s) outputs the scan data to a peripheral device.

66. A handheld intraoral scanning device according to item 64 or 65, wherein the one or more processing unit(s) is configured to pre-process the scan data and output the pre-processed scan data to a peripheral device.

67. A handheld intraoral scanning device according to items 64, 65 or 66, wherein the one or more processing unit(s) is configured to perform one, more or all of the steps of the computer implemented method according to any one of the items 1-55.

68. A handheld intraoral scanning device according to any one of items 64-67, wherein the one or more output device(s) is at least one audio device and/or at least one light-emitting device and/or at least one haptic device.

69. A handheld intraoral scanning device according to item 68, wherein the at least one audio device is a speaker.

70. A handheld intraoral scanning device according to item 68, wherein the at least one light-emitting device is a LED ring that can perform different combinations of light emission such as light pulses, increasing or decreasing light brightness, varying light colours.

71. A handheld intraoral scanning device according to item 70, wherein the brightness of the light emitted by the LED ring is correlated to the added data/information.

72. A handheld intraoral scanning device according to item 71, wherein the brightness is increased when the rate of added data is high, and wherein the brightness is decreased when the rate of added data is low.

73. A handheld intraoral scanning device according to any of the items 64-72, wherein the feedback signal correlates with the removal of an overlay present on the digital 3D representation.

The invention claimed is:

1. A 3D scanner system for providing feedback during scanning of a dental object, the 3D scanner system comprising:

an intraoral scanning device for scanning the dental object within an oral cavity, the intraoral scanning device comprising:

one or more projector units for projecting a pattern of light onto a surface of the dental object;

one or more image sensors for acquiring one or more images in response to illuminating a surface of the dental object, wherein the dental object is at least a part of a dental arch;

one or more processing units operatively coupled to the intraoral scanning device, the processing unit(s) configured for continuously, during a scanning session, performing the steps of:

-generating a digital three-dimensional (3D) representation of the dental object based on one or more scan patches, wherein the scan patches are generated based on images acquired by the image sensor(s);

updating the digital 3D representation based on registration of one or more new scan patches to said 3D representation, wherein said new scan patches at least partially overlap with the digital 3D representation; and determining the amount of overlap between the digital 3D representation and the new scan patch(es);

wherein the 3D scanner system is configured for providing a feedback signal correlating with the amount of overlap, wherein the feedback signal is an auditory signal comprising a plurality of sound pulses separated by a time delay, wherein the 3D scanner system is configured for adjusting or changing the time delay based on the determined overlap.

2. The 3D scanner system according to claim 1, wherein the 3D scanner system is configured for increasing the time delay when the determined overlap is above a predefined upper threshold.

3. The 3D scanner system according to claim 2, wherein the time delay is selected from a predefined first range when the determined overlap is above the predefined upper threshold.

4. The 3D scanner system according to claim 3, wherein the predefined first range covers the range 70 ms to 250 ms.

5. The 3D scanner system according to claim 1, wherein the 3D scanner system is configured for decreasing the time delay when the determined overlap is below a predefined lower threshold.

6. The 3D scanner system according to claim 5, wherein the time delay is selected from a predefined second range when the determined overlap is below the predefined lower threshold.

7. The 3D scanner system according to claim 6, wherein the predefined second range covers the range 10 ms to 110 ms.

8. The 3D scanner system according to claim 1, wherein the 3D scanner system is configured for continuously changing the time delay during a scanning session in response to the determined overlap between a given new scan patch and the digital 3D representation.

9. The 3D scanner system according to claim 1, wherein the processing unit(s) are further configured for generating a second digital 3D representation of the dental object based on the updated digital 3D representation.

10. The 3D scanner system according to claim 1, wherein the processing unit(s) are further configured for determining a surface area of the digital 3D representation and the updated digital 3D representation, wherein the difference in surface area between said 3D representations is determined.

11. The 3D scanner system according to claim 10, wherein the feedback signal is correlated with the difference in surface area, such that the signal is correlated with how much the surface area of the digital three-dimensional representation has expanded after the step of updating the digital 3D representation.

12. The 3D scanner system according to claim 1, wherein the processing unit(s) are configured for distinguishing between the digital 3D representation and an overlay on said digital 3D representation, wherein the processing unit(s) are further configured for removing at least a part of said overlay upon rescanning the area on the digital 3D representation having said overlay.

13. The 3D scanner system according to claim 12, wherein the feedback signal is correlated with the removal of said overlay, such that a property of the feedback signal is altered based on the rate of the removal.

14. The 3D scanner system according to claim12, wherein the 3D scanner system is configured for providing a first feedback signal correlating with the amount of overlap between the new scan patch and the digital 3D representation, and further configured for providing a second feedback signal correlating with the removal of the overlay or the rate of removal of said overlay.

15. The 3D scanner system according to claim 1, wherein the intraoral scanning device further comprises a light-emitting device configured for providing a visual feedback signal to a user operating the intraoral scanning device.

16. The 3D scanner system according to claim 15, wherein the visual feedback signal correlates with the amount of overlap, and wherein the light-emitting device is configured for changing a brightness level of the visual feedback signal based on the determined overlap and/or difference in surface area.

17. The 3D scanner system according to claim 15, wherein the light-emitting device is configured for changing a brightness level depending on the rate of which the surface area of the digital 3D representation expands or depending on whether scan patches are correctly registered.

18. The 3D scanner system according to claim 17, wherein the brightness level is decreased in case the scanner system is unable to register the new scan patch(es) to the digital 3D representation.

19. The 3D scanner system according to claim 15, wherein the light-emitting device is an LED ring extending along the circumference of the intraoral scanning device.

20. The 3D scanner system according to claim 1, wherein the scanner system further comprises a haptic device configured for providing a haptic feedback signal, wherein at least a property of the haptic feedback signal is altered based on the determined overlap or based on a difference in surface area between the digital 3D representation and the updated digital 3D representation.

21. The 3D scanner system according to claim 20, wherein the haptic device is configured for providing a vibration in case the scanner system is unable to register the new scan patch(es) to the digital 3D representation.

* * * * *